(12) United States Patent
Ocaña Fernández et al.

(10) Patent No.: US 9,808,469 B2
(45) Date of Patent: Nov. 7, 2017

(54) ANTITUMOR ACTIVITY OF MULTI-KINASE INHIBITORS IN TRIPLE NEGATIVE BREAST CANCER

(71) Applicant: ENTRECHEM, S.L, Oviedo (ES)

(72) Inventors: Alberto Ocaña Fernández, Albacete (ES); Atanasio Pandiella Alonso, Salamanca (ES); Francisco Morís Varas, Oviedo (ES)

(73) Assignee: ENTRECHEM, S.L., Oviedo (ES)

( * ) Notice: Subject to any disclaimer, the term of this patent is extended or adjusted under 35 U.S.C. 154(b) by 0 days.

(21) Appl. No.: 15/314,342

(22) PCT Filed: May 27, 2015

(86) PCT No.: PCT/EP2015/061641
§ 371 (c)(1),
(2) Date: Nov. 28, 2016

(87) PCT Pub. No.: WO2015/181201
PCT Pub. Date: Dec. 3, 2015

(65) Prior Publication Data
US 2017/0196880 A1   Jul. 13, 2017

(30) Foreign Application Priority Data

May 30, 2014  (EP) .................................. 14170596

(51) Int. Cl.
| | | |
|---|---|---|
| *A61K 31/553* | (2006.01) | |
| *A61K 31/555* | (2006.01) | |
| *A61K 31/337* | (2006.01) | |
| *A61K 31/502* | (2006.01) | |

(52) U.S. Cl.
CPC .......... *A61K 31/553* (2013.01); *A61K 31/337* (2013.01); *A61K 31/502* (2013.01); *A61K 31/555* (2013.01)

(58) Field of Classification Search
None
See application file for complete search history.

(56) References Cited

U.S. PATENT DOCUMENTS

| | | | |
|---|---|---|---|
| 5,827,846 A | 10/1998 | Regenass et al. | |
| 2011/0136753 A1 | 6/2011 | Perez Salas et al. | |

FOREIGN PATENT DOCUMENTS

| | | | | |
|---|---|---|---|---|
| EP | 2277885 A1 | * | 1/2011 | ............. C07H 19/23 |
| WO | 9532974 A1 | | 12/1995 | |
| WO | 9532975 A1 | | 12/1995 | |

OTHER PUBLICATIONS

Evers, B et al Clin Cancer Res 2008 vol. 14 pp. 3916-3927.*

Docetaxel package insert p. 1 2010 from www.accessdata.fda.gov accessed Jun. 22 2017.*
Caboplatin package insert 2010 from www.accessdata.fda.gov accessed Jun. 22 2017.*
Sánchez, César, et al.; "Generation of potent and selective kinase inhibitors by combinatorial biosynthesis of glycosylated indolocarbazoles," Chem. Commun., 2009, pp. 4118-4120.
Shi, Xuebing, et al.; "Treatment for triple-negative breast cancer," Chinese-German Journal of Clinical Oncology, 2012, pp. 539-543, vol. 11.
Fornier, MD, Monica, et al.; "The Paradox of Triple Negative Breast Cancer: Novel Approaches to Treatment," The Breast Journal, 2012, pp. 41-51, vol. 18.
Santana-Davila, Rafael, et al.; "Treatment options for patients with triple-negative breast cancer," Journal of Hematology & Oncology, 2010, pp. 1-11, vol. 3.
Anders, Carey K., et al.; "Biology, Metastatic Patterns, and Treatment of Patients with Triple-Negative Breast Cancer," Clin Breast Cancer, 2009, pp. S73-S81, vol. 9.
International Search Report/Written Opinion, dated Aug. 24, 2015.
Shipitsin, Michail, et al.; "Molecular Definition of Breast Tumor Heterogeneity," Cancer Cell, 2007, pp. 259-273, vol. 11.
Hanahan, Douglas, et al.; "Hallmarks of Cancer: The Next Generation," Cell, 2011, pp. 646-674, vol. 144.
Perou, Charles M., et al.; "Molecular portraits of human breast tumours," Nature, 2000, pp. 747-752, vol. 406.
Sørlie, Therese et al.; "Gene expression patterns of breast carcinomas distinguish tumor subclasses with clinical implications," PNAS, 2001, pp. 10869-10874, vol. 98.
Nielsen, Torsten O., et al.; "Immunohistochemical and Clinical Characterization of the Basal-Like Subtype of Invasive Breast Carcinoma," Clinical Cancer Research, 2004, pp. 5367-5374, vol. 10.
Sun, Tingting, et al.; "Activation of Multiple Proto-oncogenic Tyrosine Kinases in Breast Cancer via Loss of the PTPN12 Phosphatase," Cell, 2011, pp. 703-718, vol. 144.
Montero, JC, et al.; "Active kinase profiling, genetic and pharmacological data define mTOR as an important common target in triple-negative breast cancer," Oncogene, 2014, pp. 148-156, vol. 33; Abstract Only.

(Continued)

*Primary Examiner* — Heidi Reese
(74) *Attorney, Agent, or Firm* — Tristan A. Fuierer; Moore & Van Allen, PLLC

(57) ABSTRACT

A composition comprising
a) a compound of Formula (I), where $R_1$, $R_2$, and $R_3$ are, each one and independently, hydrogen or a protector group, wherein said protector group may consist of an alkyl group, a cycloalkyl group, a heterocyclic cycloalkyl group, a hydroxyalkyl group, a halogenated alkyl group, an alkoxyalkyl group, an alkenyl group, an alkynyl group, an aryl group, a heterocyclic aryl group, an alkylaryl group, an ester group, a carbonate group, a carboxylic acid group, an aldehyde group, a ketone group, a urethane group, a silyl group, a sulfoxide group or a combination thereof,
$R_5$, $R_6$, $R_7$, $R_8$, $R_9$ and $R_{10}$ are, each one and independently, hydrogen, hydroxyl or an —$OR_4$ group, where $R_4$ is a protector group according to the previous definition; and
b) at least one chemotherapeutic agent, suitable for use in the treatment of Breast Cancer.

7 Claims, 7 Drawing Sheets

(56) References Cited

OTHER PUBLICATIONS

Dent, Rebecca, et al.; "Triple-Negatice Breast Cancer: Clinical Features and Patterns of Recurrence," Clin Cancer Res, 2007, pp. 4429-4434, vol. 13.
Masuda, Hiroko, et al.; "Differential Response to Neoadjuvant Chemotherapy Among 7 Triple-Negatice Breast Cancer Molecular Subtypes," Clinical Cancer Research, 2013, pp. 5533-5540, vol. 19.
Lehmann, Brian D., et al.; "Identification of human triple-negative breast cancer subtypes and preclinical models for selection of targeted therapies," The Journal of Clinical investigation, 2011, pp. 2750-2767, vol. 121.
Ocaña, A., et al.; "The Evolving landscape of protein kinases in breast cancer: clinical implications," Cancer Treat Rev., 2013, pp. 68-76, vol. 39; Abstract Only.
Cleator, DR. Susan, et al.; "Triple-negative breast cancer: Therapeutic options," The Lancet Oncology, 2007, pp. P235-P244, vol. 8; Abstract Only.
Ullrich, Axel, et al.; "Signal Transduction by Receptors with Tyrosine Kinase Activity," Cell, 1990, pp. 203-212, vol. 61; Abstract Only.
Schlessinger, Joseph; "Cell Signaling by Receptor Tyrosine Kinases," Cell, 2000, pp. 211-225, vol. 103.
Balko, Justin M., et al.; "Activation of MAPK Pathways due to DUSP4 Loss Promotes Cancer Stem Cell-like Phenotypes in Basal-like Breast Cancer," Cancer Res, 2013, pp. 6346-6358, vol. 73.
Baselga, José, et al.; "Randomized Phase II Study of the Anti-Epidermal Growth Factor Receptor Monoclonal Antibody Cetuximab With Cisplatin Versus Cisplatin Alone in Patients With Metastatic Triple-Negative Breast Cancer," Journal of Clinical Oncology, 2013, pp. 2586-2592, vol. 31.
Shah, SP, et al.; "The clonal and mutational evolution spectrum of primary triple-negative breast cancers," Nature, 2012, pp. 395-399, vol. 486; Abstract Only.
Foulkes, William, D., et al.; "Germline BRCA1 Mutations and Basal Epithelial Phenotype in Breast Cancer," Journal of National Cancer Institute, 2003, pp. 1482-1485, vol. 95.
Turner, N., et al.; "Hallmarks of 'BRCAness' in sporadic cancers," Nat Rev Cancer, 2004, pp. 814-819, vol. 4; Abstract Only.
Bassi, C., et al.; "Nuclear PTEN controls DNA repair and sensitivity to genotoxic stress," Science, 2013, pp. 395-399, vol. 341.
Mendes-Pereira, Ana M., et al.; "Synthetic lethal targeting of PTEN mutant cells with PARP inhibitors," EMBO Mol. Med., 2009, pp. 315-322, vol. 1.
Seoane, Samuel, et al.; "Effect of Multikinase Inhibitors on Caspase-Independent Cell Death and DNA Damage in HER2-Overexpressing Breast Cancer Cells," J. Natl. Cancer Inst., 2010, pp. 1432-1446, vol. 102.
Marotta, Lauren, L.C., et al.; "The JAK2/STAT3 signaling pathway is required for growth of CD44+CD24 stem cell- like breast cancer cells in human tumors," The Journal of Clinical Investigation, 2011, pp. 2723-2735, vol. 121.
Chou, Ting-Chao, et al.; "Drug Combination Studies and Their Synergy Quantification Using the Chou-Talalay Method," Cancer Res, 2010, pp. 440-446, vol. 70.
Kastan, MB, et al.; "The many substrates and function of ATM," Nat Rev Mol Cell Biol., 2000; pp. 179-186, vol. 1; Abstract Only.
Matsuoka, Shuhei, et al.; "Ataxia telangiectasia-mutated phosphorylates Chk2 in vivo and in vitro," PNAS, 2000, pp. 10389-10394, vol. 97.

* cited by examiner

A

B

A

B

SEQUENCE LISTING

```
<160> NUMBER OF SEQ ID NOS: 20

<210> SEQ ID NO 1
<211> LENGTH: 20
<212> TYPE: DNA
<213> ORGANISM: Artificial Sequence
<220> FEATURE:
<223> OTHER INFORMATION: Synthetic Construct

<400> SEQUENCE: 1
caatgacccc ttcattgacc                                                   20

<210> SEQ ID NO 2
<211> LENGTH: 20
<212> TYPE: DNA
<213> ORGANISM: Artificial Sequence
<220> FEATURE:
<223> OTHER INFORMATION: Synthetic Construct

<400> SEQUENCE: 2
gatctcgctc ctggaagatg                                                   20

<210> SEQ ID NO 3
<211> LENGTH: 20
<212> TYPE: DNA
<213> ORGANISM: Artificial Sequence
<220> FEATURE:
<223> OTHER INFORMATION: Synthetic Construct

<400> SEQUENCE: 3
gcagccccaa agataattga                                                   20

<210> SEQ ID NO 4
<211> LENGTH: 20
<212> TYPE: DNA
<213> ORGANISM: Artificial Sequence
<220> FEATURE:
<223> OTHER INFORMATION: Synthetic Construct

<400> SEQUENCE: 4
tggcaaatca aagtggttca                                                   20

<210> SEQ ID NO 5
<211> LENGTH: 20
<212> TYPE: DNA
<213> ORGANISM: Artificial Sequence
<220> FEATURE:
<223> OTHER INFORMATION: Synthetic Construct
```

<400> SEQUENCE: 5
ggaggaagtg ctcagcaaag                                               20

<210> SEQ ID NO 6
<211> LENGTH: 20
<212> TYPE: DNA
<213> ORGANISM: Artificial Sequence
<220> FEATURE:
<223> OTHER INFORMATION: Synthetic Construct

<400> SEQUENCE: 6
tggatcaggg tgaagtggat                                               20

<210> SEQ ID NO 7
<211> LENGTH: 20
<212> TYPE: DNA
<213> ORGANISM: Artificial Sequence
<220> FEATURE:
<223> OTHER INFORMATION: Synthetic Construct

<400> SEQUENCE: 7
actctggggc tctgtcttca                                               20

<210> SEQ ID NO 8
<211> LENGTH: 20
<212> TYPE: DNA
<213> ORGANISM: Artificial Sequence
<220> FEATURE:
<223> OTHER INFORMATION: Synthetic Construct

<400> SEQUENCE: 8
ggtggtacat gcacagttgc                                               20

<210> SEQ ID NO 9
<211> LENGTH: 20
<212> TYPE: DNA
<213> ORGANISM: Artificial Sequence
<220> FEATURE:
<223> OTHER INFORMATION: Synthetic Construct

<400> SEQUENCE: 9
ccaatgcctc gtaacaacct                                               20

<210> SEQ ID NO 10
<211> LENGTH: 20
<212> TYPE: DNA
<213> ORGANISM: Artificial Sequence
<220> FEATURE:
<223> OTHER INFORMATION: Synthetic Construct

<400> SEQUENCE: 10
agctcttcac cctgcaaaaa                                               20

<210> SEQ ID NO 11
<211> LENGTH: 20
<212> TYPE: DNA
<213> ORGANISM: Artificial Sequence
<220> FEATURE:
<223> OTHER INFORMATION: Synthetic Construct

<400> SEQUENCE: 11
gtgaccacca ttcggctact                                               20

```
<210> SEQ ID NO 12
<211> LENGTH: 20
<212> TYPE: DNA
<213> ORGANISM: Artificial Sequence
<220> FEATURE:
<223> OTHER INFORMATION: Synthetic Construct

<400> SEQUENCE: 12
tcaaggacaa acccaccttc                                               20

<210> SEQ ID NO 13
<211> LENGTH: 20
<212> TYPE: DNA
<213> ORGANISM: Artificial Sequence
<220> FEATURE:
<223> OTHER INFORMATION: Synthetic Construct

<400> SEQUENCE: 13
ggactcagtt ccaacccaaa                                               20

<210> SEQ ID NO 14
<211> LENGTH: 20
<212> TYPE: DNA
<213> ORGANISM: Artificial Sequence
<220> FEATURE:
<223> OTHER INFORMATION: Synthetic Construct

<400> SEQUENCE: 14
gctagtccac tggcttctgg                                               20

<210> SEQ ID NO 15
<211> LENGTH: 20
<212> TYPE: DNA
<213> ORGANISM: Artificial Sequence
<220> FEATURE:
<223> OTHER INFORMATION: Synthetic Construct

<400> SEQUENCE: 15
gtctgggcct ggattttgta                                               20

<210> SEQ ID NO 16
<211> LENGTH: 20
<212> TYPE: DNA
<213> ORGANISM: Artificial Sequence
<220> FEATURE:
<223> OTHER INFORMATION: Synthetic Construct

<400> SEQUENCE: 16
tgccccaaag atgaagaaag                                               20

<210> SEQ ID NO 17
<211> LENGTH: 20
<212> TYPE: DNA
<213> ORGANISM: Artificial Sequence
<220> FEATURE:
<223> OTHER INFORMATION: Synthetic Construct

<400> SEQUENCE: 17
ctcttcatag cccccatcag                                               20

<210> SEQ ID NO 18
<211> LENGTH: 20
<212> TYPE: DNA
<213> ORGANISM: Artificial Sequence
<220> FEATURE:
<223> OTHER INFORMATION: Synthetic Construct
```

```
<400> SEQUENCE: 18
aatccctgca caacgatctc                                              20

<210> SEQ ID NO 19
<211> LENGTH: 19
<212> TYPE: DNA
<213> ORGANISM: Artificial Sequence
<220> FEATURE:
<223> OTHER INFORMATION: Synthetic Construct

<400> SEQUENCE: 19
agttttggga atgcattgg                                               19

<210> SEQ ID NO 20
<211> LENGTH: 20
<212> TYPE: DNA
<213> ORGANISM: Artificial Sequence
<220> FEATURE:
<223> OTHER INFORMATION: Synthetic Construct

<400> SEQUENCE: 20
tcggcagctg ttgtatcttg                                              20
```

ANTITUMOR ACTIVITY OF MULTI-KINASE INHIBITORS IN TRIPLE NEGATIVE BREAST CANCER

CROSS-REFERENCE TO RELATED APPLICATIONS

This application is filed under the provisions of 35 U.S.C. §371 and claims the priority of International Patent Application No. PCT/EP2015/061641, filed on 27 May 2015 entitled "ANTITUMOR ACTIVITY OF MULTI-KINASE INHIBITORS IN TRIPLE NEGATIVE BREAST CANCER" in the name of Alberto OCAÑA FERNÁNDEZ et al., which claims priority to European Patent Application No. 14170596.2 filed on 30 May 2014, both of which are hereby incorporated by reference herein in their entirety.

FIELD OF THE INVENTION

The present invention relates to the provision of a composition comprising a) a novel multi-kinase inhibitor; and b) at least one chemotherapeutic agent. The present invention additionally relates to use of said composition in the prevention and/or treatment of triple negative breast cancer. Furthermore, the present invention also discloses a pharmaceutical composition comprising the aforementioned composition and a method for its production.

BACKGROUND TO THE INVENTION

Breast cancer is a heterogeneous disease as demonstrated at a genomic level with the description of different breast cancer subtypes with independent clinical outcome [Cancer Cell 2007; 11: 259-273, Cell 2011; 144: 646-674, Nature 2000; 406: 747-752, Proc. Natl. Acad. Sci. U.S.A. 2001; 98: 10869-10874]. Among them, triple negative breast cancer (TNBC) refers to breast cancer that lacks expression of the estrogen receptor (ER), the progesterone receptor (PR) and the Her2/neu ($HER_2$) receptor, and represents 15% of all breast tumors [Clin. Cancer Res. 2004; 10: 5367-5374]. In TNBC, several membrane and intracellular kinases may be concomitantly activated [Cell 2011; 144: 703-718, Oncogene 2013; 33:148-156]. The PI3K/mTOR and the MAPK pathway are commonly phosphorylated in this tumor type [Oncogene 2013; 33:148-156]. Less frequently activated kinases include STAT1, STAT3 or SRC, among others [Oncogene 2013; 33:148-156]. It is associated with a specific tumor relapse pattern and an increased sensitivity to chemotherapy [Clin. Cancer Res. 2007; 13: 4429-4434, Clin. Cancer Res. 2013; 19: 5533-5540]. By using gene expression analyses it has been classified into seven subtypes with different sensitivities to treatment [J. Clin. Invest. 2011; 121: 2750-2767, Clin. Cancer Res. 2013; 19: 5533-5540]. Although the identification of these different subtypes represents a major advance in cancer, unfortunately the implementation of this classification for therapeutic purposes is unclear [J. Clin. Invest. 2011; 121: 2750-2767]. Therefore, available therapeutic options for patients with TNBC are restricted to standard treatment with chemotherapy [Clin. Cancer Res. 2013; 19: 5533-5540, Cancer Treat. Rev. 2013; 39: 68-76] and the prognosis of TNBC patients is poor due to the limited therapeutic options and the lack of specific targeted agents [Lancet Oncol. 2007; 8: 235-244].

Receptor tyrosine kinases (RTKs) and downstream pathways are involved in the regulation of many cellular functions including proliferation and survival [Cell 2011; 144: 703-718, Oncogene 2014; 33: 148-156, Cell 1990; 61: 203-212, Cell 2000; 103: 211-225] and play a central role in the genesis and/or promotion of different breast cancer subtypes tumors including the triple negative subtype. Using human samples the inventors and other research groups evaluated the kinase profile of TNBCs, observing that a number of RTKs are activated; such as the epidermal growth factor receptor (EGFR), the fibroblast growth factor receptor (FGFR) or the platelet-derived growth factor receptor (PDGFR), among others [Oncogene 2014; 33: 148-156]. In addition, several components of the PI3K/mTOR pathway were phosphorylated in a significant proportion of patients [Oncogene 2014; 33: 148-156, Cancer Res. 2013; 73: 6346-6358]. Interestingly, inhibition of the PI3K route produced a proliferative arrest in cellular models and a growth reduction in tumors implanted in xenografted animals or generated using transgenic models [Oncogene 2014; 33: 148-156]. Of note, clinical studies evaluating drugs targeting single receptors have shown disappointing results suggesting that therapeutic strategies should be designed to inhibit a number of key oncogenic nodes [J. Clin. Oncol. 2013; 31: 2586-2592]. In addition, different studies including those using sequencing approaches have shown the relevance of some components of these signaling routes including the PI3K/mTOR pathway [Cell 2011; 144: 703-718, Nature 2012; 486: 395-399]. Based on the global importance of the activation of RTKs and downstream pathways in TNBC, the development of novel multi-kinase inhibitors that could present polypharmacology against key oncogenic nodes is a main goal and tyrosine kinase inhibitors (TKIs) designed to neutralize their function are in clinical development.

Alterations of the DNA repair machinery seem to be of great significance in this cancer subtype, and particularly in basal-like breast tumors [J. Natl. Cancer Inst. 2003; 95: 1482-1485, Nat. Rev. Cancer 2004; 4: 814-819]. This subgroup is enriched with genes associated with proliferation and DNA damage response, when evaluated by gene expression analyses [J. Clin. Invest. 2011; 121: 2750-2767]. It is enriched with somatic and acquired mutations in DNA repair genes, mainly BRCA1 and BRCA2, involved in the homologous recombination (HR) repair mechanism [Nat. Rev. Cancer 2004; 4: 814-819]. The association between RTKs or its downstream pathways with DNA repair mechanisms is unclear. However, activation of some routes like the PI3K/mTOR pathway has been linked with DNA repair and sensitivity to genotoxic stress [Science 2013; 341: 395-9, EMBO Mol. Med. 2009; 1: 315-322]. In addition, treatment with some TKIs alone or in combination induces DNA damage. Indeed, administration of the multi-tyrosine kinase inhibitor dasatinib, with the anti-$HER_2$ antibody trastuzumab, induced DNA damage, and synergized with chemotherapy [J. Natl. Cancer Inst. 2010; 102: 1432-1446]. Since basal-like tumors show an increase in proliferation and an impairment of DNA repair mechanisms, it would be desirable to identify drugs that would induce DNA damage in addition to providing an anti-proliferative effect.

It is the problem of the present invention to provide improved means of preventing and/or treating TNBC which not only induces DNA damage in said tumors, but also provides an anti-proliferative, tumor-specific effect, such that it does not exhibit adverse side effects.

BRIEF DESCRIPTION OF THE INVENTION

The present invention relates to a composition comprising a) a compound of Formula (I)

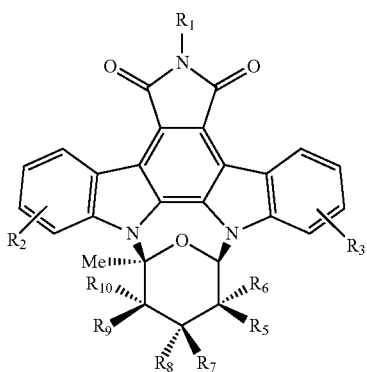

Formula (I)

where
R₁, R₂, and R₃ are, each one and independently, hydrogen or a protector group, which may consist of an alkyl group, a cycloalkyl group, a heterocyclic cycloalkyl group, a hydroxyalkyl group, a halogenated alkyl group, an alkoxyalkyl group, an alkenyl group, an alkynyl group, an aryl group, a heterocyclic aryl group, an alkylaryl group, an ester group, a carbonate group, a carboxylic acid group, an aldehyde group, a ketone group, a urethane group, a silyl group, a sulfoxide group or a combination thereof, R₅, R₆, R₇, R₈, R₉ and R₁₀ are, each one and independently, hydrogen, hydroxyl or an —OR₄ group, where R₄ is a protector group according to the previous definition; and b) at least one chemotherapeutic agent.

In a preferred embodiment, the composition of the present invention comprises a compound of Formula (I) selected from Formula (II), Formula (III) and Formula (IV):

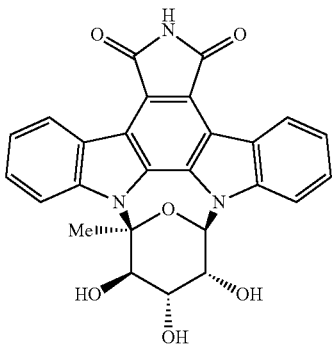

Formula (II)

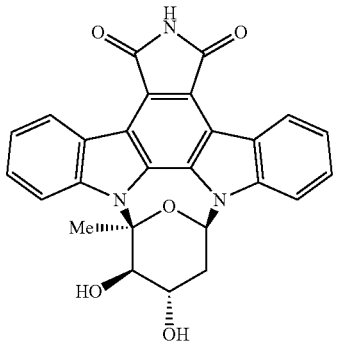

Formula (III)

Throughout the present specification the compound of Formula (III) has been used for exemplifying the claimed effects.

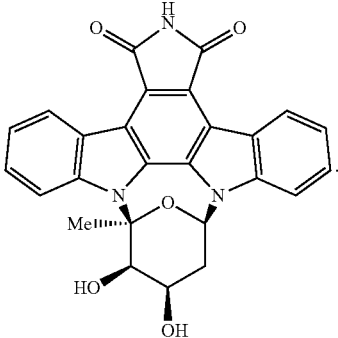

Formula (IV)

In another preferred embodiment of the present invention, the at least one chemotherapeutic agent is a chemotherapeutic agent used for breast cancer, preferably selected from platinum-based antineoplastic agents, anti-mitotic chemotherapeutic agents or inhibitors of the enzyme poly adenosine diphosphate ribose polymerase (PARP).

In yet another preferred embodiment of the present invention, the at least one chemotherapeutic agent is a platinum-based antineoplastic agent selected from cisplatin, carboplatin, oxaliplatin, satraplatin, picoplatin, nedaplatin, triplatin and lipoplatin, more preferably cisplatin or carboplatin.

Alternatively, in another preferred embodiment of the present invention, the at least one chemotherapeutic agent is an anti-mitotic chemotherapeutic agent selected from taxanes and vinca alkaloids, more preferably selected from vinorelbine, docetaxel, paclitaxel, vinblastine and vincristine, furthermore preferably vinorelbine or docetaxel.

Furthermore, in another alternative preferred embodiment of the present invention, the at least one chemotherapeutic agent is a poly adenosine diphosphate ribose polymerase (PARP) inhibitor selected from olaparib, rucaparib and veliparib, more preferably olaparib.

The present invention also relates to a composition, as described herein, for use in the prevention and/or treatment of triple-negative breast cancer in a patient.

In addition, the present invention also relates to a use of a composition, as described herein, in the manufacture of a medicament for the prevention and/or treatment of breast cancer, preferably triple-negative breast cancer.

Moreover, the present invention also relates to a pharmaceutical composition comprising
a) a compound of Formula (I), as described herein; and
b) at least one chemotherapeutic agent.

Furthermore, the present invention relates to a method for producing a pharmaceutical composition according to any of claim 14 or 15, which comprises mixing:
a) a compound of Formula (I), as described herein; and
b) at least one chemotherapeutic agent.

A last embodiment of the invention is to provide a method of prevention and/or treatment of patients suffering from breast cancer, preferably triple-negative breast cancer, which comprises the administration to a patient in need of or to a subject with risk of suffering from breast cancer, preferably triple-negative breast cancer, of an effective dose or amount of the combination of active compounds of the invention or of a composition comprising the same, particularly represented by the combination of a compound of formula I, and most preferably of a compound selected from formula (II), formula (III) or formula (IV); with at least one chemotherapeutic agent, wherein the at least one chemotherapeutic agent is a platinum-based antineoplastic agent selected from cisplatin, carboplatin, oxaliplatin, satraplatin, picoplatin, nedaplatin, triplatin and lipoplatin, more preferably cisplatin or carboplatin; an anti-mitotic chemotherapeutic agent selected from taxanes and vinca alkaloids, more preferably selected from vinorelbine, docetaxel, paclitaxel, vinblastine and vincristine, furthermore preferably vinorelbine or docetaxel; or a PARP inhibitor selected from olaparib, rucaparib and veliparib, more preferably olaparib.

DETAILED DESCRIPTION OF THE INVENTION

Figure 1:
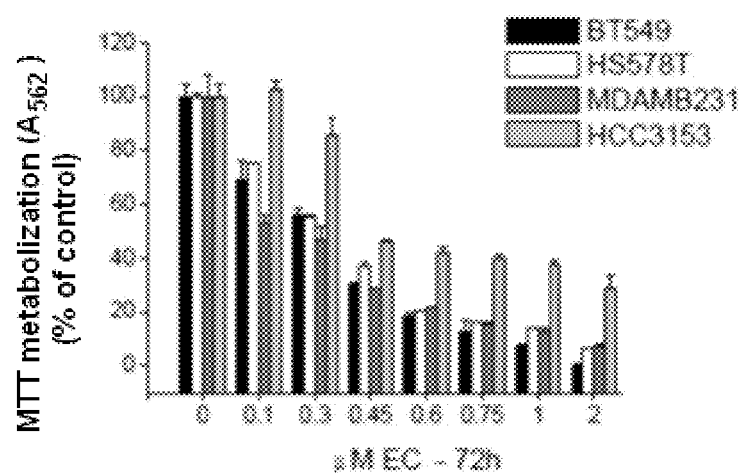
FIG. 1. A. Dose-dependent anti-proliferative effect of Formula (III) (EC) on HS578T, BT549 and MDA-MB-231 (MDAMB231) cells cultured in DMEM 10% FBS, and on HCC3153 cells cultured in RPMI 10% FBS, determined as percentage of MTT metabolism [metabolization, measured as a function of absorbance at 562 nm ($A_{562}$)] at doses of from 0 to 2 µM after 72 h; B. Time-dependent anti-proliferative effect of Formula (III) (500 nM) on HS578T, BT549 and MDA-MB-231 (MDAMB231) cells cultured in DMEM 10% FBS, and on HCC3153 cells cultured in RPMI 10% FBS, determined as percentage of MTT metabolism [metabolization, measured as a function of absorbance at 562 nm ($A_{562}$)] over 6 days.
Figure 1:
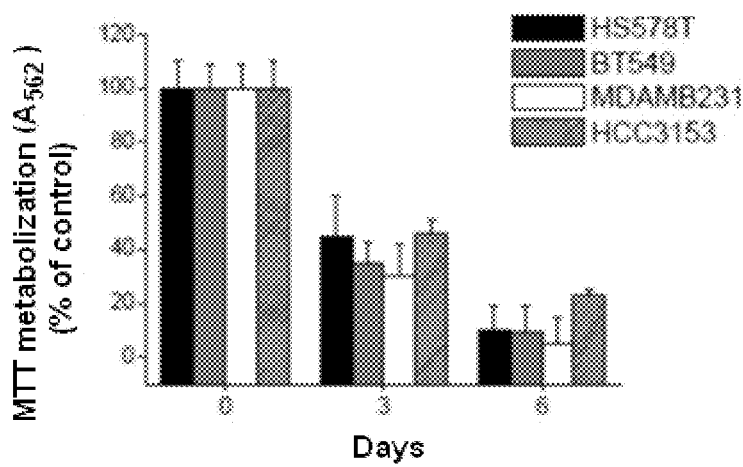

The present invention relates to a composition comprising a) a compound of Formula (I)

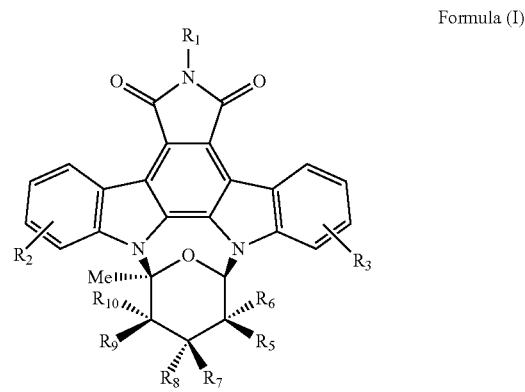

Formula (I)

where
$R_1$, $R_2$, and $R_3$ are, each one and independently, hydrogen or a protector group, wherein said protector group may consist of an alkyl group, a cycloalkyl group, a heterocyclic cycloalkyl group, a hydroxyalkyl group, a halogenated alkyl group, an alkoxyalkyl group, an alkenyl group, an alkynyl group, an aryl group, a heterocyclic aryl group, an alkylaryl group, an ester group, a carbonate group, a carboxylic acid group, an aldehyde group, a ketone group, a urethane group, a silyl group, a sulfoxide group or a combination thereof, $R_5$, $R_6$, $R_7$, $R_8$, $R_9$ and $R_{10}$ are, each one and independently, hydrogen, hydroxyl or an —$OR_4$ group, where $R_4$ is a protector group according to the previous definition; and
b) at least one chemotherapeutic agent.

Preferably, the composition of the present invention comprises a compound of Formula (I) where $R_1$, $R_2$, and $R_3$ are hydrogen, $R_9$ is OH, $R_{10}$ is hydrogen, and $R_5$, $R_6$, $R_7$ and $R_8$ are, each one and independently, hydrogen, hydroxyl or an —$OR_4$ group, where $R_4$ is a protector group selected from an alkyl group, a cycloalkyl group, a heterocyclic cycloalkyl group, a hydroxyalkyl group, a halogenated alkyl group, an alkoxyalkyl group, an alkenyl group, an alkynyl group, an aryl group, a heterocyclic aryl group, an ester group, a carboxylic acid group, an aldehyde group, a ketone group, a silyl group, a sulfoxide group or a combination thereof.

In the present invention the $R_4$ protector group is preferably selected from an alkyl group, a cycloalkyl group, a halogenated alkyl group, an alkenyl group, an alkynyl group, an aryl group, a heterocyclic aryl group, an aldehyde group, a sulfoxide group or a combination thereof, more preferably an alkyl group, a cycloalkyl group, a halogenated alkyl group, an alkenyl group, an alkynyl group, or a combination thereof, furthermore preferably an alkyl group.

Still more preferably, the composition of the present invention comprises a compound of Formula (I) where $R_1$, $R_2$, and $R_3$ are hydrogen, $R_9$ is OH, $R_{10}$ is hydrogen, and $R_5$, $R_6$, $R_7$ and $R_8$ are, each one and independently, hydrogen or hydroxyl. Furthermore preferably, the composition of the present invention comprises a compound of Formula (I) where $R_1$, $R_2$, and $R_3$ are hydrogen, $R_9$ is OH and $R_{10}$ is hydrogen, wherein one of $R_7$ or $R_8$ is hydrogen, and the other is hydroxyl, and $R_5$ and $R_6$ are, each one and independently, hydrogen or hydroxyl.

In a preferred embodiment the composition of the present invention comprises a compound of Formula (I) selected from Formula (II), Formula (III) and Formula (IV):

Formula (II)

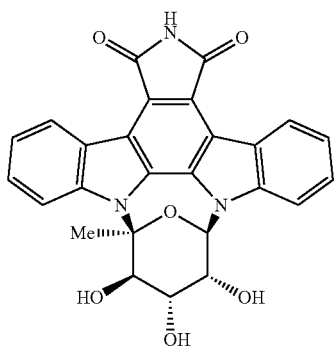

Formula (III)

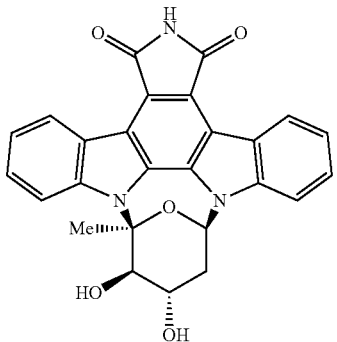

Formula (IV)

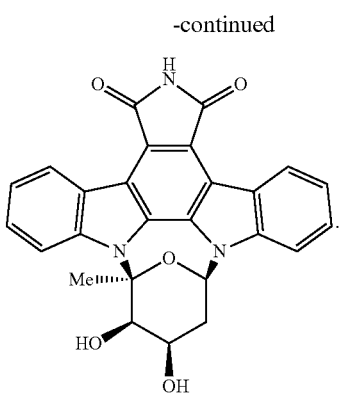

Formula (III) is one such hybrid indolocarbazole molecule falling under the structure herein defined by Formula (I). Formula (III) is obtained from genetically modified bacteria by combinatorial biosynthesis of Rebeccamycin and Staurosporine biosynthesis pathways and produced by fermentation [Chem. Commun. (Camb.) 2009: 4118-20]. Formula (III) shows affinity towards and inhibits the activity of a range of tyrosine and serine/threonine kinases in biochemical assays at the nanomolar and subnanomolar range, shows antitumoral activity in a wide range of solid tumors both in proliferation and sphere assays, and inhibits key signaling nodes at submicromolar range, concentrations well below plasmatic levels in experimental animals. Thus, Formula (III) is a multikinase inhibitor, more specifically a serine/threonine kinase inhibitor. Studies in animal models showed the anti-tumoral activity of Formula (III) in vivo with no evidence of toxicities. In fact, Formula (III) has completed its safety evaluation in animals and is about to initiate its clinical development. Nevertheless, the limited specificity of Formula (III) led to the inhibition of relevant pathways like the JAK/STAT route that is involved in the genesis of breast tumors with stem cell properties [J. Clin. Invest. 2011; 121:2723-2735].

In another preferred embodiment, the present invention comprises a composition, according to any of the foregoing, wherein the at least one chemotherapeutic agent is a chemotherapeutic agent suitable for use in treating breast cancer. In a further preferred embodiment, the at least one chemotherapeutic agent is selected from platinum-based antineoplastic agents, anti-mitotic chemotherapeutic agents or PARP inhibitors. PARP inhibitors are a group of pharmacological inhibitors of the enzyme poly adenosine diphosphate ribose polymerase, also known as poly ADP ribose polymerase (PARP).

In other preferred embodiments of the present invention, the composition comprises at least one chemotherapeutic agent, wherein said at least one chemotherapeutic agent is:
a) a platinum-based antineoplastic agent selected from cisplatin, carboplatin, oxaliplatin, satraplatin, picoplatin, nedaplatin, triplatin tetranitrate and lipoplatin;
b) an anti-mitotic chemotherapeutic agent selected from taxanes and vinca alkaloids; and/or
c) a PARP inhibitor selected from olaparib, rucaparib and veliparib.

In another preferred embodiment, the present invention comprises a composition according to any of the foregoing, wherein the at least one chemotherapeutic agent is cisplatin or carboplatin. In yet another preferred embodiment, the present invention comprises a composition, according to any of the foregoing, wherein the at least one chemotherapeutic agent is selected from vinorelbine, docetaxel, paclitaxel, vinblastine, vindesine and vincristine, furthermore preferably vinorelbine or docetaxel. In still another preferred embodiment, the present invention comprises a composition, according to any of the foregoing, wherein the at least one chemotherapeutic agent is olaparib.

Preferably, the at least one chemotherapeutic agent, according to any of the foregoing, is selected from cisplatin, carboplatin, vinorelbine, docetaxel and olaparib. Alternatively, the at least one chemotherapeutic agent, according to any of the foregoing, is selected from cisplatin, carboplatin and docetaxel. The at least one chemotherapeutic agent, according to any of the foregoing, may also be selected from carboplatin and docetaxel.

Thus, one preferred embodiment relates to a composition comprising
a) a compound of Formula (I), where $R_1$, $R_2$, and $R_3$ are hydrogen, $R_9$ is OH, $R_{10}$ is hydrogen, and $R_5$, $R_6$, $R_7$ and $R_8$ are, each one and independently, hydrogen or hydroxyl; and
b) at least one chemotherapeutic agent selected from cisplatin, carboplatin, nedaplatin, lipoplatin, vinorelbine, docetaxel, paclitaxel, vinblastine, vindesine, vincristine and olaparib.

Another preferred embodiment relates to a composition comprising
a) a compound of Formula (I) where $R_1$, $R_2$, and $R_3$ are hydrogen, $R_9$ is OH and $R_{10}$ is hydrogen, wherein one of $R_7$ or $R_8$ is hydrogen, and the other is hydroxyl, and $R_5$ and $R_6$ are, each one and independently, hydrogen or hydroxyl; and
b) at least one chemotherapeutic agent selected from cisplatin, carboplatin, lipoplatin, vinorelbine, docetaxel, paclitaxel, vinblastine, vindesine and olaparib.

The present invention also relates to a composition, according to any of the foregoing, for use in the prevention and/or treatment of breast cancer in a patient. In other words, the present invention also relates to the use of a composition, according to any of the foregoing, in the manufacture of a medicament for the prevention and/or treatment of breast cancer. Preferably, said breast cancer is triple-negative breast cancer (TNBC). TNBC refers to a breast cancer that does not express the genes for the estrogen receptor, progesterone receptor and Her2/neu.

The present invention also relates to a pharmaceutical composition comprising
a) a compound of Formula (I) according to any of the foregoing; and
b) at least one chemotherapeutic agent.

Another preferred embodiment of the present invention comprises a method for producing any of the aforementioned pharmaceutical compositions, which comprises mixing:
a) a compound of Formula (I) according to the foregoing; and
b) at least one chemotherapeutic agent.

Said method may additionally involve a step of heating, agitation, centrifugation and/or filtration in order to ensure homogeneity of the resulting mixture.

Examples of the compositions of the present invention and representative processes for their isolation, use, and manufacture appear below, but should not be construed to limit the invention.

EXAMPLES

I) Material and Methods
a) Cell Culture and Drug Compounds

Hs578T, BT549 and MDA-MB-231 were grown in DMEM and HCC3153 in RPMI; both mediums were purchased from Sigma Aldrich, supplemented with 10% FBS, 100 mU/mL penicillin, 100 µg/mL streptomycin and 2 mM L-glutamine, in a 5% $CO_2$ atmosphere at 37° C. These triple negative breast cancer cell lines were obtained from the American Type Culture Collection Cell Biology Collection (ATCC) (Manassas, Va.). The medium was changed every 2 days.

For three-dimensional cell culture, the bottom of 24 multi-dish plates was covered with a thin ice-cold 4% Matrigel (BD Biosciences) layer and incubated at 37° C. for 20 minutes to allow the Matrigel to solidify. Matrigel was added to conventional DMEM. The desired cells were tripsinized (0.25% trypsin-EDTA solution (2.5 g/L of trypsin, 0.38 g/L of EDTA) collected and resuspended to a final concentration of 12.500 cls/mL in 2% Matrigel. The cell suspension was added over the solidified Matrigel layer and incubated at 37° C. The medium was changed after 4 days and the cell culture was daily visualized under a microscope for phenotype monitoring. The cells were cultured for 10 days.

The multi-tyrosine kinase inhibitor Formula (III) was provided by Entrechem S.L. Cisplatin, carboplatin, docetaxel and vinorelbine were purchased from Selleckchem. Olaparib was purchased from/provided by?

b) MTT Metabolization

Cell proliferation and growth experiments were carried out using 3-(4,5-dimethylthiazol-2-yl)-2,5-diphenyltetrazolium bromide (MTT) uptake assays, where MTT is reduced to purple formazan by the mitochondria of living cells. Increase in cell number is detected by augmented MTT metabolization, and decrease in cell number is reflected by a decrease. HS578T, BT549, MDA-MB-231 and HCC3153 cells were plated at a density of $1 \times 10^4$ cells per well in 24-well plates and cultured overnight in DMEM supplemented with 10% FBS. The cells were treated with the drug at different concentrations to plot the dose-response curves in all cancer cell lines using in the study. Time-response curve was performed using the $IC_{50}$ dose of 500 nM. After treatment, each well was replaced with 250 µL of fresh medium containing MTT (0.5 µg/mL) and incubated for 1 hour. The medium was then removed and 500 µL of dimethyl sulfoxide was added to each well. The plate was agitated in the dark for 5 minutes to dissolve the MTT-formazan crystals. The absorbance of the samples was recorded at 562 nm in a multi-well plate reader (BMG labtech). Results were plotted as the mean values of quadruplicates from a representative experiment that was repeated at least two independent times.

To determine whether Formula (III) combined to other chemotherapy drugs was synergistic, additive, or antagonist, the CalcuSyn v2.0 software programme (Biosoft, Ferguson, Mo.) was used. This program allows the calculation of the combination index (CI) based on the algorithm of Chou and Talalay [Cancer Res. 2010; 70: 440-446]. Combination index values less than 1 indicate synergism, values equal to 1 indicate an additive effect, whereas values greater than 1 indicate antagonism. Combination index values from three independent experiments were generated.

c) Cell Cycle and Apoptosis Assays

Cell cycle analyses and evaluation of apoptosis were performed by flow cytometry using propidium iodide and Annexin V, respectively.

For cell cycle analyses, HS578T, BT549 and MDA-MB-231 cells were cultured in 100-mm culture dishes, grown to 70% confluence, and treated with 500 nM Formula (III) for 24 h. Cell monolayers were then incubated in trypsin-EDTA and resuspended in 1 mL of PBS. After three washes with PBS, the cell pellets were resuspended in ice cold 70% ethanol for 2 min and centrifuged 5 min at 1800 rpm. The cell pellets were treated with 1 mL of propidium iodide (PI) staining solution (PBS containing 50 µg/mL of PI, 0.5% Tween 20, 0.1 µg/mL RNase A) (BD Biosciences) and incubated in the dark for 1 h. DNA content and cell cycle analyses were performed by using a FACS canto II flow cytometer and the CellQuest software (BD Biosciences).

For apoptosis analyses, HS578T, BT549 and MDA-MB-231 cell monolayers were incubated in trypsin-EDTA, washed twice with cold PBS, and then resuspended in binding buffer (10 mM HEPES free acid [pH 7.4], 140 mM NaCl, 2.5 mM $CaCl_2$) at a concentration of $1 \times 10^6$ cells per mL. A total of $1 \times 10^5$ cells were incubated for 15 minutes in the dark with Annexin V-APC (BD Biosciences) and propidium iodide (PI) staining solution (5 µL Annexin V-fluorescein isothiocyanate, 10 µL of PI [5 µL/mL final concentration], 400 µL binding buffer).

d) Western Blotting and Antibody Array

Western-blot and phospho-array kits were used for evaluation of signaling intermediates.

HS578T and BT549 cell lines were grown in DMEM 10% of FBS and at 70% confluence were treated with Formula (III) at 500 nM for 6, 12 and 24 hours. Cells were washed with phosphate-buffered saline (PBS) (137 mM NaCl, 2.7 mM KCl, 8 mM $Na_2HPO_4$, 1.5 mM $KH_2PO_4$) and lysed in ice-cold lysis buffer (20 mM Tris-HCl [pH 7.0], 140 mM NaCl, 50 mM EDTA, 10% glycerol, 1% Nonidet P-40, 1 µM pepstatin, 1 µg/mL aprotinin, 1 µg/mL leupeptin, 1 mM phenylmethyl sulfonyl fluoride, 1 mM sodium orthovanadate). Lysates were centrifuged at 10000 g at 4° C. for 10 minutes. The protein level in the supernatants was quantified using BCA protein assay (Sigma Aldrich). A total of 50 µg of protein of each sample was used for analysis. Samples were then boiled in electrophoresis sample buffer and placed on 6%-15% sodium dodecyl sulfate-polyacrylamide gel electrophoresis (SDS-PAGE) gels, depending on the molecular weight of the proteins to be analyzed. Briefly, after electrophoresis, proteins in gels were transferred to polyvinylidene difluoride membranes (Millipore Corporation). Membranes were blocked in Tris-buffered saline with Tween (TBST) (100 mM Tris [pH 7.5], 150 mM NaCl, 0.05% Tween 20) containing 1% of bovine serum albumin for 1 h and then incubated overnight with the corresponding antibody. Anti-pS473-AKT and anti-pT308-AKT were purchased from Santa Cruz; Anti-pS6, anti-pSTAT3 and anti-GADPH were purchased from Cell Signalling Technology; Anti-pH3, were purchased from Millipore-Cell Signaling; anti-p-H2AX were purchased from BD Biosciences. After washing with TBST, membranes were incubated with HRP-conjugated anti-mouse or anti-rabbit secondary antibodies (1:5000 dilution) for 1 hour and bands were visualized by using ECL Plus Western Blotting Detection System (GE Healthcare, Buckinghamshire, United Kingdom).

To perform the dot blot analyses with commercial arrays, two human phospho-RTK array kits were used following the respective manufacturers instructions. The Human Phospho-Kinase Array (Catalog ARY003B) detects the relative site-specific phosphorylation of 43 intracellular kinases. The Phospho-Receptor Tyrosine Kinase (RTK) Array Kit (Catalog ARY001B) detects the phosphorylation of 49 different RTKs.

e) Microarray Analysis of mRNA

MDA-MB-231 cells were grown in DMEM with 10% of FBS, and when 70% confluent, cells were treated with 500 nM Formula (III) for 24 h. Total RNA was extracted and purified using the RNeasy Mini Kit (Qiagen). Double-stranded cDNA and biotinylated cRNA were synthesized using a T7-polyT primer and the BioArray RNA labeling kit (Enzo Life Sciences, Farmingdale, N.Y.), respectively. The labeled RNA was fragmented and hybridized to human oligonucleotide arrays (Human Gene ST Arrays) (Affymetrix, Santa Clara, Calif.) according to manufacturers instructions. For the microarray data analysis, Affymetrix CEL files from each of the two microarray hybridization experiments for the two conditions [untreated control and treated with 500 nM Formula (III)] were imported into the dChip software (Dana Farber Cancer Institute, Boston, Mass.). Normalization of all arrays was done against the array with median overall intensity. Genes with different expression values from the control vs treated group were obtained. The list of genes was analyzed using functional annotation bioinformatics microarray analysis (DAVID), and gene set enrichment analyses (GSEA). Some functions were then visualized using Cytoscape software. Thus, gene-set enrichment analyses were performed to identify relevant functions effected by the drug and the identified genes were confirmed by RT-PCR.

f) Real-Time Quantitative Reverse-Transcriptase (RT)-PCR

Total RNA was extracted from cells with Rneasy Mini Kit (QIAGEN) as recommended by the supplier. cDNAs were synthesized from 3 mg of total RNA by using RevertAid H Minus First Strand cDNA synthesis Kit (Fermentas) in a total volume of 12 mL. Reverse transcription was performed at 42° C. for 60 min, followed by 10 min at 70° C. for inactivation. Real-time PCR analysis was carried out with 4.2 mL cDNA using Fast SYBR Green Master Mix (Applied Biosystems) in StepOnePlus Real-Time PCR system (Applied Biosystems) according to the manufacturer's instructions. Samples were analyzed in triplicate and mRNA expression was normalized to GADPH rRNA and quantified by the comparative cycle threshold (Ct) method. PCRs were done using the following specific primers (SEQ ID NO: 1 to SEQ ID NO: 20):

|  |  |
|---|---|
| GADPH forward | (SEQ ID NO: 1) CAATGACCCCTTCATTGACC |
| GADPH reverse | (SEQ ID NO: 2) GATCTCGCTCCTGGAAGATG |
| XPA forward | (SEQ ID NO: 3) GCAGCCCCAAAGATAATTGA |
| XPA reverse | (SEQ ID NO: 4) TGGCAAATCAAAGTGGTTCA |
| GADD45 forward | (SEQ ID NO: 5) GGAGGAAGTGCTCAGCAAAG |
| GADD45 reverse | (SEQ ID NO: 6) TGGATCAGGGTGAAGTGGAT |
| BRCA1 forward | (SEQ ID NO: 7) ACTCTGGGGCTCTGTCTTCA |
| BRCA1 reverse | (SEQ ID NO: 8) GGTGGTACATGCACAGTTGC |
| BRCA2 forward | (SEQ ID NO: 9) CCAATGCCTCGTAACAACCT |
| BRCA2 reverse | (SEQ ID NO: 10) AGCTCTTCACCCTGCAAAAA |
| DDB2 forward | (SEQ ID NO: 11) GTGACCACCATTCGGCTACT |
| DDB2 reverse | (SEQ ID NO: 12) TCAAGGACAAACCCACCTTC |

-continued

| | |
|---|---|
| FANCE forward | (SEQ ID NO: 13)<br>GGACTCAGTTCCAACCCAAA |
| FANCE reverse | (SEQ ID NO: 14)<br>GCTAGTCCACTGGCTTCTGG |
| LIG4 forward | (SEQ ID NO: 15)<br>GTCTGGGCCTGGATTTTGTA |
| LIG4 reverse | (SEQ ID NO: 16)<br>TGCCCCAAAGATGAAGAAAG |
| PRMT6 forward | (SEQ ID NO: 17)<br>CTCTTCATAGCCCCCATCAG |
| PRMT6 reverse | (SEQ ID NO: 18)<br>AATCCCTGCACAACGATCTC |
| RAD52 forward | (SEQ ID NO: 19)<br>AGTTTTGGGAATGCATTGG |
| RAD52 reverse | (SEQ ID NO: 20)<br>TCGGCAGCTGTTGTATCTTG |

The PCR cycling conditions were as follows: 95° C. for 10 min; then 40 cycles at 95° C. for 30 s and 60° C. for 1 min.

g) Xenograft Studies

In vivo antitumoral effects were evaluated using xenografted animals. Mice were handled at the animal facility following legal guidelines. Female BALB/c nude mice, 7 weeks old were obtained from Janvier Labs. After 15 days quarantine, $2-5 \times 10^7$ MDA-MB-231 cells in 100 μL of PBS with 20% Matrigel were injected into the mammary fat pads of mice. Two weeks after the injection, mice were randomly assigned into two groups (with equal average tumor volumes before initiation of treatments): control (n=5) and Formula (III) (n=5). After approximately 2 weeks, when tumors reached a volume of 150 mm³ treatment was initiated. Animals were inhalatorily anaesthetized and then treated with Formula (III). Tumors diameters and tumor growth inhibition were measured every three days. Tumor volumes were calculated using the following formula: $V=(L \times W^2)/2$, where V=volume (cubic millimeters), L=length (millimeters) and W=width (millimeters). Mice were killed by $CO_2$ inhalation on day 24 after initiation of treatments.

II) Results a) Antitumor Effect of Formula (III)

To explore the effect of Formula (III) on proliferation, a panel of TNBC cell lines which included HS578T, BT549 and MDA-MB-231 were used. Treatment with Formula (III) inhibited the MTT metabolization in a dose and time dependent manner (FIGS. 1A, 1B). Doses in the submicromolar (nanomolar) range were able to produce more than 80% of growth inhibition (i.e. reduced proliferation) in all cell lines studied.

Figure 2:
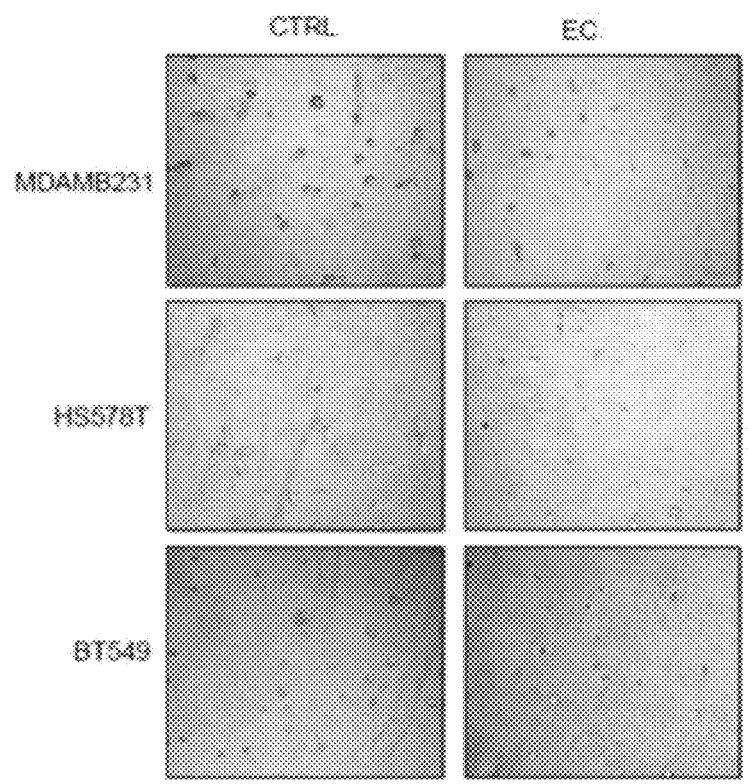
FIG. 2. A. Effect of Formula (III) (EC) on spherical structure formation in HS578T, BT549 and MDA-MB-231 (MDAMB231) cultures in matrigel, a semisolid medium where cells grow forming spherical structures. B. Effect of Formula (III) (EC) on the diameter in arbitrary units (AU) of spherical structures formed in HS578T, BT549 and MDA-MB-231 (MDAMB231) cultures in matrigel.
Figure 2:
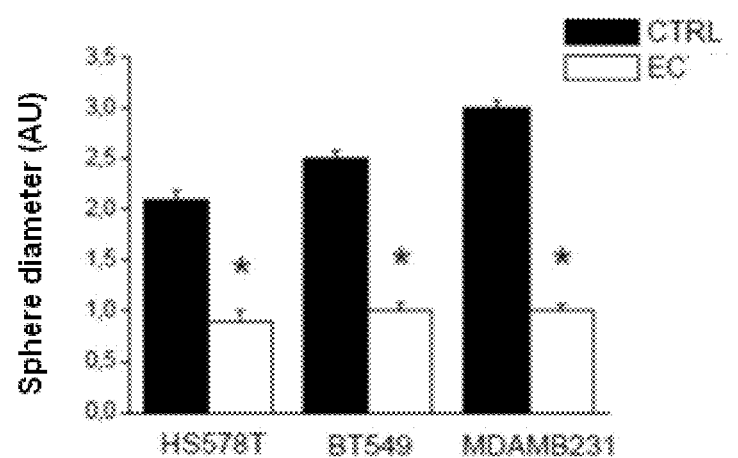

The effect of Formula (III) on three-dimensional growth was next investigated. For this purpose, HS578T, BT549 and MDA-MB-231 were cultured in matrigel, a semisolid medium where cells grow forming spherical structures (FIG. 2A). Treatment with Formula (III) strongly decreased the diameter of these spheres, demonstrating the effect of Formula (III) on the inhibition of cell growth (FIG. 2B).

b) Effect of Formula (III) in Combination with Chemotherapy Agents

Figure 3:
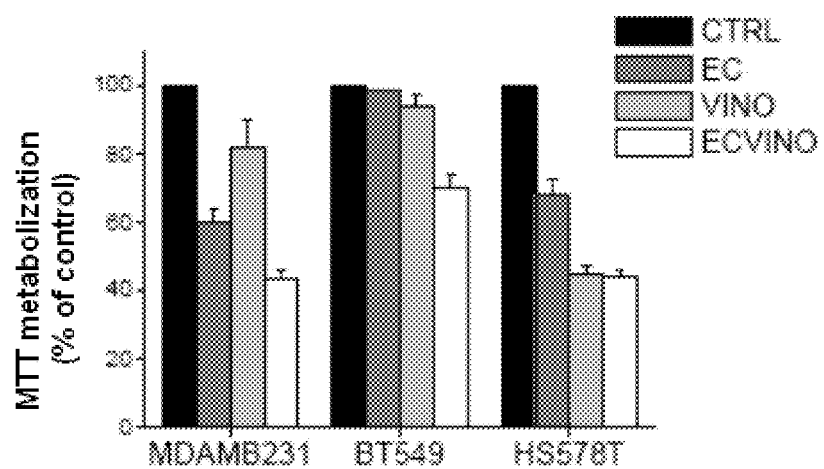
FIG. 3. Anti-proliferative effect on HS578T, BT549 and MDA-MB-231 (MDAMB231) cells cultured in DMEM 10% FBS, measured as percentage of MTT metabolism (metabolization) with respect to an untreated control (CTRL, for which the mean absorbance values of untreated samples from each cell line were taken as 100%) of A. fixed dose administration over 72 hours of Formula (III) (EC), vinorelbine (VINO), or a combination thereof (ECVINO); B. fixed dose administration over 72 hours of Formula (III) (EC), docetaxel (DOC), or a combination thereof (ECDOC); and C. fixed dose administration over 72 hours of Formula (III) (EC), carboplatin (CARBO), or a combination thereof (ECCARBO).
Figure 3:
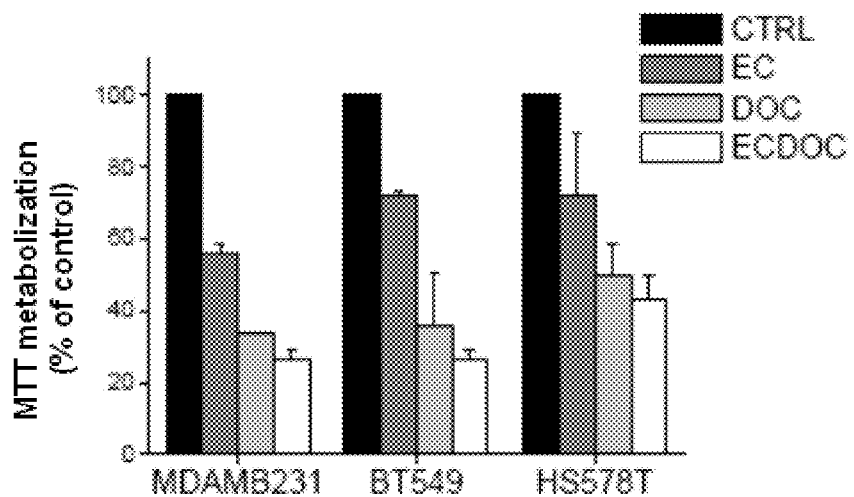
Figure 3:
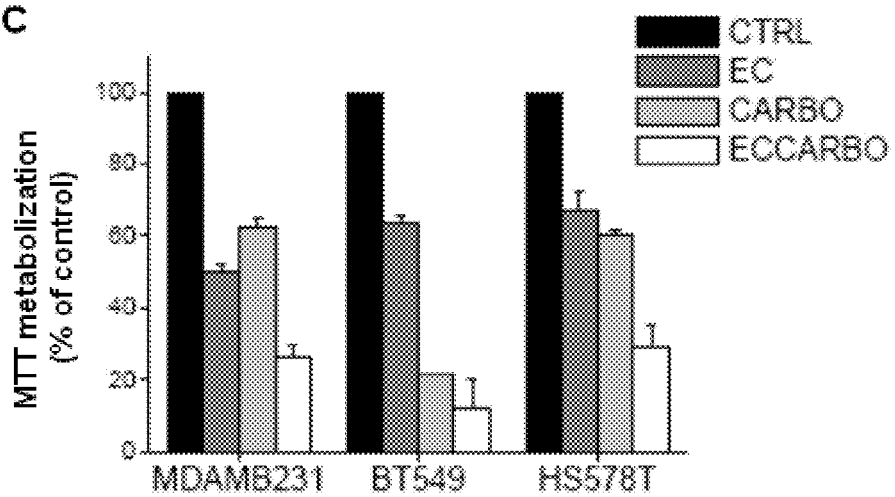

As success in cancer therapy is based on drug combinations, the effect of Formula (III) in association with chemotherapy agents used in the clinical setting for triple negative tumors, including vinorelbine, docetaxel, and platinum compounds (cisplatin and carboplatin), was investigated. A dose response curve was first obtained for these chemotherapies in order to select doses around the $IC_{50}$. Next, Formula (III) was combined with these agents (cf. Tables 1-15). In general, administration of Formula (III) with vinorelbine, carboplatin and docetaxel, using a fixed dose, increased the anti-proliferative effect of each agent given alone (FIG. 3A-1C).

Figure 4:
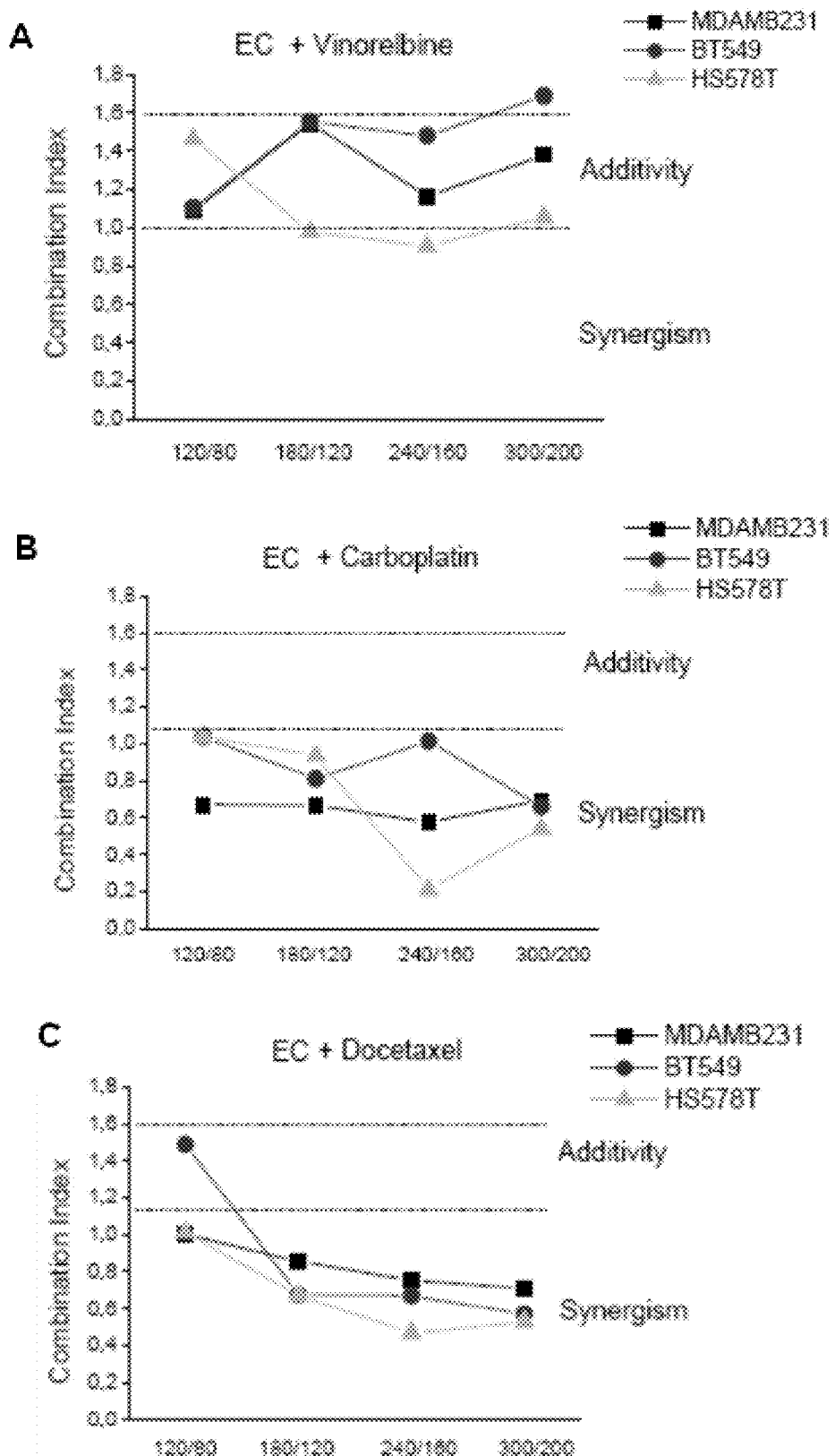
FIG. 4. Combination indices calculated using Calcusyn software for HS578T (triangles), BT549 (circles) and MDA-MB-231 (MDAMB231, squares) cells with A. combined doses of Formula (III) (EC) in the nanomolar range with doses of vinorelbine [x-axis=concentration of Formula (III) (EC) (nM)/concentration of vinorelbine (nM)]; B. combined doses of Formula (III) (EC) in the nanomolar range with doses of carboplatin [x-axis=concentration of Formula (III) (EC) (nM)/concentration of carboplatin (nM)]; and C. combined doses of Formula (III) (EC) in the nanomolar range with doses of docetaxel [x-axis=concentration of Formula (III) (EC) (nM)/concentration of docetaxel (nM)].

To identify synergistic interactions several doses of Formula (III) in the nanomolar range were combined with doses of these agents around or below the $IC_{50}$ in HS578T, BT549 and MDA-MB-231. For this purpose the Chou-Talay algorithm for combination index analysis [Cancer Res. 2010; 70: 440-446] was used. Combinations with vinorelbine were not synergistic in MDA-MB-231 and BT549 (cf. Tables 3 and 8), and only for some doses in HS578T (cf. Table 13 and FIG. 4A). By contrast all doses for carboplatin were strongly synergistic in the three cell lines (cf. Tables 1, 6 and 11, and FIG. 4B). Similarly, combinations with docetaxel were synergistic in most of the studied doses (cf. Tables 4, 9 and 14, and FIG. 4C). Those results demonstrate that synergism of the compositions of present invention with cancer chemotherapy agents was unexpected either qualitatively with regard to the type of chemotherapy compounds or, when synergism did appear, also quantitatively, for each one of any of the chemotherapy agents comprised in the compositions of invention, to be considered for synergistic combination.

TABLE 1

Effect of Formula (III), Carboplatin and combinations thereof on inhibition of MDA-MB-231 cell proliferation.

| Quantity of drug | | | Percentage inhibition | | | | | | | |
|---|---|---|---|---|---|---|---|---|---|---|
| | | | Formula (III) | | Carboplatin | | Formula (III) + Carboplatin | | | |
| Formula (III) (nM) | Carboplatin (nM) | Formula (III) (nM) + Carboplatin (nM) | mean | s.d. | mean | s.d. | mean | s.d. | Combination Index | Ratio Formula (III)/Carboplatin |
| 0 | 0 | 0 | 100.00 | 5.64 | 100.00 | 5.64 | 100.00 | 5.64 | | |
| 120 | 80 | 120 + 80 | 63.77 | 7.75 | 74.70 | 4.85 | 38.35 | 1.89 | 0.67 | 1.5 |
| 180 | 120 | 180 + 120 | 49.75 | 2.69 | 62.30 | 2.48 | 26.27 | 3.33 | 0.67 | 1.5 |
| 240 | 160 | 240 + 160 | 38.25 | 0.33 | 61.11 | 4.31 | 16.38 | 1.88 | 0.58 | 1.5 |
| 300 | 200 | 300 + 200 | 28.13 | 0.65 | 58.21 | 3.48 | 15.56 | 3.19 | 0.69 | 1.5 |

TABLE 2

Effect of Formula (III), Cisplatin and combinations thereof on inhibition of MDA-MB-231 cell proliferation.

| Quantity of drug | | | Percentage inhibition | | | | | | |
|---|---|---|---|---|---|---|---|---|---|
| | | | Formula (III) | | Cisplatin | | Formula (III) + Cisplatin | | |
| Formula (III) (nM) | Cisplatin (nM) | Formula (III) (nM) + Cisplatin (nM) | mean | s.d. | mean | s.d. | mean | s.d. | Combination Index | Ratio Formula (III)/Cisplatin |
| 0 | 0 | 0 | 100.00 | 5.64 | 100.00 | 5.64 | 100.00 | 5.64 | | |
| 120 | 80 | 120 + 80 | 63.77 | 7.75 | 91.74 | 6.21 | 56.53 | 4.11 | 1.16 | 1.5 |
| 180 | 120 | 180 + 120 | 49.75 | 2.69 | 71.66 | 3.42 | 49.62 | 1.98 | 1.47 | 1.5 |
| 240 | 160 | 240 + 160 | 38.25 | 0.33 | 69.26 | 0.50 | 33.70 | 1.40 | 1.31 | 1.5 |
| 300 | 200 | 300 + 200 | 28.13 | 0.65 | 68.95 | 0.17 | 15.42 | 4.33 | 0.89 | 1.5 |

TABLE 3

Effect of Formula (III), Vinorelbine and combinations thereof on inhibition of MDA-MB-231 cell proliferation.

| Quantity of drug | | | Percentage inhibition | | | | | | | |
|---|---|---|---|---|---|---|---|---|---|---|
| | | | Formula (III) | | Vinorelbine | | Formula (III) + Vinorelbine | | | |
| Formula (III) (nM) | Vinorelbine (nM) | Formula (III) (nM) + Vinorelbine (nM) | mean | s.d. | mean | s.d. | mean | s.d. | Combination Index | Ratio Formula (III)/Vinorelbine |
| 0 | 0 | 0 | 100.00 | 3.06 | 100.00 | 3.06 | 100.00 | 3.06 | | |
| 200 | 1 | 200 + 1 | 60.32 | 4.06 | 81.71 | 8.10 | 43.22 | 2.82 | 1.09 | 200 |
| 260 | 1.3 | 260 + 1.3 | 54.53 | 3.24 | 58.44 | 1.38 | 46.98 | 3.43 | 1.55 | 200 |
| 300 | 1.6 | 300 + 1.6 | 49.39 | 6.14 | 58.67 | 9.77 | 28.34 | 3.39 | 1.17 | 187.5 |
| 380 | 1.9 | 380 + 1.9 | 36.89 | 4.28 | 48.51 | 1.67 | 27.08 | 4.48 | 1.38 | 200 |

TABLE 4

Effect of Formula (III), Docetaxel and combinations thereof on inhibition of MDA-MB-231 cell proliferation.

| Quantity of drug | | | Percentage inhibition | | | | | | | |
|---|---|---|---|---|---|---|---|---|---|---|
| | | | Formula (III) | | Docetaxel | | Formula (III) + Docetaxel | | | |
| Formula (III) (nM) | Docetaxel (nM) | Formula (III) (nM) + Docetaxel (nM) | mean | s.d. | mean | s.d. | mean | s.d. | Combination Index | Ratio Formula (III)/Docetaxel |
| 0 | 0 | 0 | 100.00 | 2.87 | 100.00 | 2.87 | 100.00 | 2.87 | | |
| 100 | 0.4 | 100 + 0.4 | 56.37 | 4.95 | 59.33 | 4.97 | 43.74 | 0.67 | 1.00 | 250 |
| 200 | 0.8 | 200 + 0.8 | 56.35 | 2.41 | 33.75 | 0.13 | 26.54 | 2.39 | 0.86 | 250 |
| 300 | 1.2 | 300 + 1.2 | 40.19 | 2.15 | 25.29 | 0.78 | 17.90 | 0.37 | 0.75 | 250 |
| 400 | 1.6 | 400 + 1.6 | 35.26 | 3.28 | 25.28 | 0.34 | 13.47 | 0.41 | 0.71 | 250 |

TABLE 5

Effect of Formula (III), Olaparib and combinations thereof on inhibition of MDA-MB-231 cell proliferation.

| Quantity of drug | | | Percentage inhibition | | | | | | | |
|---|---|---|---|---|---|---|---|---|---|---|
| | | | Formula (III) | | Olaparib | | Formula (III) + Olaparib | | | |
| Formula (III) (nM) | Olaparib (nM) | Formula (III) (nM) + Olaparib (nM) | mean | s.d. | mean | s.d. | mean | s.d. | Combination Index | Ratio Formula (III)/Olaparib |
| 0 | 0 | 0 | 100.00 | 8.56 | 100.00 | 8.56 | 100.00 | 8.56 | | |
| 100 | 10 | 100 + 10 | 62.54 | 4.67 | 66.94 | 6.46 | 45.75 | 1.19 | 0.52 | 10 |
| 200 | 20 | 200 + 20 | 46.90 | 2.96 | 58.28 | 0.27 | 25.58 | 0.37 | 0.32 | 10 |
| 300 | 30 | 300 + 30 | 40.53 | 0.48 | 57.33 | 1.66 | 18.58 | 1.15 | 0.29 | 10 |
| 400 | 40 | 400 + 40 | 33.70 | 0.01 | 57.03 | 1.62 | 18.74 | 0.74 | 0.39 | 10 |

TABLE 6

Effect of Formula (III), Carboplatin and combinations thereof on inhibition of BT-549 cell proliferation.

| Quantity of drug | | | Percentage inhibition | | | | | | Ratio |
|---|---|---|---|---|---|---|---|---|---|
| | | | Formula (III) | | Carboplatin | | Formula (III) + Carboplatin | | Formula |
| Formula (III) (nM) | Carboplatin (nM) | Formula (III) (nM) + Carboplatin (nM) | mean | s.d. | mean | s.d. | mean | s.d. | Combination Index | (III)/ Carboplatin |
| 0 | 0 | | 100.00 | 8.66 | 100.00 | 8.66 | 100.00 | 8.66 | | |
| 120 | 80 | 120 + 80 | 75.49 | 3.62 | 37.09 | 2.38 | 25.89 | 9.56 | 1.04 | 1.5 |
| 180 | 120 | 180 + 120 | 63.69 | 1.80 | 21.43 | 0.23 | 12.16 | 7.96 | 0.81 | 1.5 |
| 240 | 160 | 240 + 160 | 44.98 | 1.24 | 19.39 | 5.74 | 11.19 | 0.32 | 1.01 | 1.5 |
| 300 | 200 | 300 + 200 | 31.92 | 0.39 | 15.69 | 1.86 | 4.58 | 7.13 | 0.66 | 1.5 |

TABLE 7

Effect of Formula (III), Cisplatin and combinations thereof on inhibition of BT-549 cell proliferation

| Quantity of drug | | | Percentage inhibition | | | | | | | |
|---|---|---|---|---|---|---|---|---|---|---|
| | | | Formula (III) | | Cisplatin | | Formula (III) + Cisplatin | | Combination | Ratio |
| Formula (III) (nM) | Cisplatin (nM) | Formula (III) (nM) + Cisplatin (nM) | mean | s.d. | mean | s.d. | mean | s.d. | Index | Formula (III)/Cisplatin |
| 0 | 0 | | 100.00 | 8.66 | 100.00 | 8.66 | 100.00 | 8.66 | | |
| 120 | 80 | 120 + 80 | 75.49 | 3.62 | 63.96 | 5.29 | 49.25 | 0.03 | 1.26 | 1.5 |
| 180 | 120 | 180 + 120 | 63.69 | 1.80 | 46.37 | 3.85 | 39.10 | 2.01 | 1.54 | 1.5 |
| 240 | 160 | 240 + 160 | 44.98 | 1.24 | 38.19 | 1.98 | 22.87 | 1.56 | 1.41 | 1.5 |
| 300 | 200 | 300 + 200 | 31.92 | 0.39 | 19.56 | 4.94 | 13.10 | 0.71 | 1.27 | 1.5 |

TABLE 8

Effect of Formula (III), Vinorelbine and combinations thereof on inhibition of BT-549 cell proliferation

| Quantity of drug | | | Percentage inhibition | | | | | | | |
|---|---|---|---|---|---|---|---|---|---|---|
| | | | Formula (III) | | Vinorelbine | | Formula (III) + Vinorelbine | | Combination | Ratio |
| Formula (III) (nM) | Vinorelbine (nM) | Formula (III) (nM) + Vinorelbine (nM) | mean | s.d. | mean | s.d. | mean | s.d. | Index | Formula (III)/Vinorelbine |
| 0 | 0 | 0 | 100.00 | 9.00 | 100.00 | 9.00 | 100.00 | 9.00 | | |
| 200 | 1 | 200 + 1 | 98.48 | 0.11 | 94.16 | 3.11 | 69.99 | 4.17 | 1.11 | 200 |
| 260 | 1.3 | 260 + 1.3 | 92.90 | 3.58 | 91.71 | 0.99 | 76.47 | 5.91 | 1.55 | 200 |
| 300 | 1.6 | 300 + 1.6 | 78.02 | 1.98 | 74.36 | 3.22 | 55.70 | 1.80 | 1.48 | 187.5 |
| 380 | 1.9 | 380 + 1.9 | 75.85 | 1.97 | 62.84 | 3.77 | 48.07 | 4.92 | 1.69 | 200 |

TABLE 9

Effect of Formula (III), Docetaxel and combinations thereof on inhibition of BT-549 cell proliferation

| Quantity of drug | | | Percentage inhibition | | | | | | | |
|---|---|---|---|---|---|---|---|---|---|---|
| | | | Formula (III) | | Docetaxel | | Formula (III) + Docetaxel | | Combination | Ratio |
| Formula (III) (nM) | Docetaxel (nM) | Formula (III) (nM) + Docetaxel (nM) | mean | s.d. | mean | s.d. | mean | s.d. | Index | Formula (III)/Docetaxel |
| 0 | 0 | 0 | 100.00 | 7.51 | 100.00 | 7.51 | 100.00 | 7.51 | | |
| 100 | 0.4 | 100 + 0.4 | 68.75 | 6.81 | 82.04 | 4.65 | 68.41 | 12.15 | 1.49 | 250 |
| 200 | 0.8 | 200 + 0.8 | 72.14 | 1.41 | 36.11 | 14.39 | 26.46 | 2.85 | 0.68 | 250 |
| 300 | 1.2 | 300 + 1.2 | 55.86 | 3.99 | 36.45 | 4.44 | 17.46 | 2.77 | 0.67 | 250 |
| 400 | 1.6 | 400 + 1.6 | 36.26 | 1.26 | 36.13 | 1.17 | 10.45 | 1.20 | 0.57 | 250 |

TABLE 10

Effect of Formula (III), Olaparib and combinations thereof on inhibition of BT-549 cell proliferation

| Quantity of drug | | | Percentage inhibition | | | | | | | |
|---|---|---|---|---|---|---|---|---|---|---|
| | | | Formula (III) | | Olaparib | | Formula (III) + Olaparib | | Combination | Ratio |
| Formula (III) (nM) | Olaparib (nM) | Formula (III) (nM) + Olaparib (nM) | mean | s.d. | mean | s.d. | mean | s.d. | Index | Formula (III)/Olaparib |
| 0 | 0 | 0 | 100.00 | 7.73 | 100.00 | 7.73 | 100.00 | 7.73 | | |
| 100 | 10 | 100 + 10 | 90.84 | 7.25 | 81.09 | 5.02 | 84.18 | 6.85 | 1.71 | 10 |
| 200 | 20 | 200 + 20 | 71.37 | 0.58 | 77.20 | 3.63 | 60.99 | 1.43 | 1.33 | 10 |
| 300 | 30 | 300 + 30 | 62.75 | 6.10 | 74.16 | 7.24 | 31.32 | 4.14 | 0.83 | 10 |
| 400 | 40 | 400 + 40 | 38.46 | 1.48 | 45.10 | 3.15 | 20.86 | 3.77 | 0.77 | 10 |

TABLE 11

Effect of Formula (III), Carboplatin and combinations thereof on inhibition of HS578T cell proliferation.

| Quantity of drug | | | Percentage inhibition | | | | | | | Ratio |
|---|---|---|---|---|---|---|---|---|---|---|
| | | | Formula (III) | | Carboplatin | | Formula (III) + Carboplatin | | Combination | Formula (III)/ |
| Formula (III) (nM) | Carboplatin (nM) | Formula (III) (nM) + Carboplatin (nM) | mean | s.d. | mean | s.d. | mean | s.d. | Index | Carboplatin |
| 0 | 0 | | 100.00 | 8.45 | 100.00 | 8.45 | 100.00 | 8.45 | | |
| 120 | 80 | 120 + 80 | 74.88 | 6.57 | 70.90 | 6.75 | 50.03 | 7.27 | 1.04 | 1.5 |
| 180 | 120 | 180 + 120 | 67.47 | 4.70 | 60.26 | 1.59 | 29.33 | 5.88 | 0.94 | 1.5 |
| 240 | 160 | 240 + 160 | 50.84 | 2.81 | 50.49 | 7.80 | 1.70 | 4.64 | 0.21 | 1.5 |
| 300 | 200 | 300 + 200 | 46.83 | 4.43 | 24.33 | 1.35 | 6.00 | 4.45 | 0.54 | 1.5 |

TABLE 12

Effect of Formula (III), Cisplatin and combinations thereof on inhibition of HS578T cell proliferation

| Quantity of drug | | | Percentage inhibition | | | | | | | |
|---|---|---|---|---|---|---|---|---|---|---|
| | | | Formula (III) | | Cisplatin | | Formula (III) + Cisplatin | | Combination | Ratio |
| Formula (III) (nM) | Cisplatin (nM) | Formula (III) (nM) + Cisplatin (nM) | mean | s.d. | mean | s.d. | mean | s.d. | Index | Formula (III)/Cisplatin |
| 0 | 0 | | 100.00 | 8.45 | 100.00 | 8.45 | 100.00 | 8.45 | | |
| 120 | 80 | 120 + 80 | 74.88 | 6.57 | 78.97 | 2.60 | 64.30 | 4.58 | 1.11 | 1.5 |
| 180 | 120 | 180 + 120 | 67.47 | 4.70 | 66.89 | 3.10 | 40.60 | 0.60 | 0.69 | 1.5 |
| 240 | 160 | 240 + 160 | 50.84 | 2.81 | 66.34 | 0.91 | 34.01 | 6.68 | 0.72 | 1.5 |
| 300 | 200 | 300 + 200 | 46.83 | 4.43 | 65.19 | 4.13 | 21.34 | 8.81 | 0.53 | 1.5 |

TABLE 13

Effect of Formula (III), Vinorelbine and combinations thereof on inhibition of HS578T cell proliferation

| Quantity of drug | | | Percentage inhibition | | | | | | | Ratio |
|---|---|---|---|---|---|---|---|---|---|---|
| | | | Formula (III) | | Vinorelbine | | Formula (III) + Vinorelbine | | Combination | Formula (III)/ |
| Formula (III) (nM) | Vinorelbine (nM) | Formula (III) (nM) + Vinorelbine (nM) | mean | s.d. | mean | s.d. | mean | s.d. | Index | Vinorelbine |
| 0 | 0 | 0 | 100.00 | 7.15 | 100.00 | 7.15 | 100.00 | 7.15 | | |
| 200 | 1 | 200 + 1 | 67.80 | 4.96 | 44.90 | 2.43 | 44.18 | 2.16 | 1.46 | 200 |
| 260 | 1.3 | 260 + 1.3 | 59.94 | 3.02 | 40.04 | 1.48 | 33.73 | 4.96 | 0.98 | 200 |
| 300 | 1.6 | 300 + 1.6 | 52.24 | 0.58 | 38.48 | 0.34 | 29.29 | 0.08 | 0.91 | 187.5 |
| 380 | 1.9 | 380 + 1.9 | 48.91 | 0.27 | 36.67 | 1.33 | 28.99 | 1.42 | 1.06 | 200 |

TABLE 14

Effect of Formula (III), Docetaxel and combinations thereof on inhibition of HS578T cell proliferation

| Quantity of drug | | | Percentage inhibition | | | | | | Ratio |
|---|---|---|---|---|---|---|---|---|---|
| | | | Formula (III) | | Docetaxel | | Formula (III) + Docetaxel | | |
| Formula (III) (nM) | Docetaxel (nM) | Formula (III) (nM) + Docetaxel (nM) | mean | s.d. | mean | s.d. | mean | s.d. | Combination Index | Formula (III)/Docetaxel |
| 0 | 0 | 0 | 100.00 | 4.54 | 100.00 | 4.54 | 100.00 | 4.54 | | |
| 100 | 0.4 | 100 + 0.4 | 76.19 | 0.35 | 73.02 | 2.67 | 63.38 | 2.84 | 1.01 | 250 |
| 200 | 0.8 | 200 + 0.8 | 72.37 | 17.19 | 49.65 | 9.03 | 43.24 | 6.83 | 0.67 | 250 |
| 300 | 1.2 | 300 + 1.2 | 66.27 | 0.15 | 45.83 | 0.51 | 29.78 | 0.66 | 0.47 | 250 |
| 400 | 1.6 | 400 + 1.6 | 57.40 | 0.99 | 47.86 | 1.69 | 27.13 | 1.38 | 0.53 | 250 |

TABLE 15

Effect of Formula (III), Olaparib and combinations thereof on inhibition of HS578T cell proliferation

| Quantity of drug | | | Percentage inhibition | | | | | | Ratio |
|---|---|---|---|---|---|---|---|---|---|
| | | | Formula (III) | | Olaparib | | Formula (III) + Olaparib | | |
| Formula (III) (nM) | Olaparib (nM) | Formula (III) (nM) + Olaparib (nM) | mean | s.d. | mean | s.d. | mean | s.d. | Combination Index | Formula (III)/Olaparib |
| 0 | 0 | 0 | 100.00 | 4.31 | 100.00 | 4.31 | 100.00 | 4.31 | | |
| 100 | 10 | 100 + 10 | 93.48 | 4.49 | 89.66 | 4.32 | 83.31 | 2.57 | 1.14 | 10 |
| 200 | 20 | 200 + 20 | 77.62 | 0.12 | 77.84 | 1.50 | 52.72 | 4.47 | 0.62 | 10 |
| 300 | 30 | 300 + 30 | 72.28 | 1.37 | 73.05 | 0.79 | 45.64 | 18.89 | 0.73 | 10 |
| 400 | 40 | 400 + 40 | 66.61 | 2.64 | 70.62 | 4.75 | 35.56 | 1.43 | 0.68 | 10 | c) Effects on Cell Cycle and Apoptosis

To identify the mechanism of action of Formula (III), the effect of the drug on cell cycle and induction of apoptosis was explored. To this end HS578T, BT549 and MDA-MB-231 were treated with Formula (III) at 500 nM or Formula (III) in combination with a chemotherapeutic agent analyzed using flow after incubation. It was observed that Formula (III) induced a strong arrest in G2/M phase, more pronounced at 24 h (15%, 22% and 18% increase for HS578T, BT549 and MDA_MB231, respectively, FIG. 5A).

Figure 5:
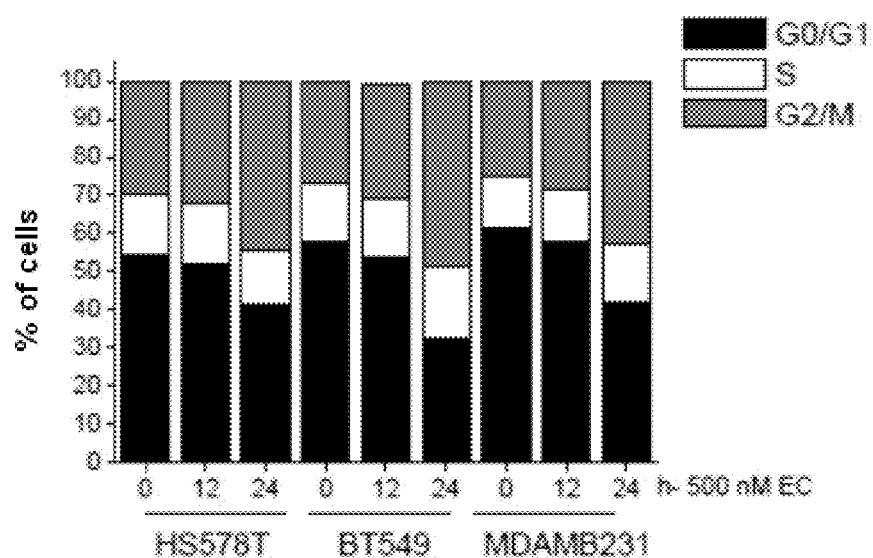
FIG. 5. Flow cytometry analysis of effect of Formula (III) (EC) (500 nM) in HS578T, BT549 and MDA-MB-231 cells cultured in DMEM 10% FBS on A. cell cycle measured as mean percentage of cells of the different phases (G0/G1, S and G2/M) of cell cycle progression measured by flow cytometry after 12 and 24 hours treatment and staining with propidium iodide (PI); B. apoptosis measured as mean percentage of cells positive or negative to Annexin staining from three independent experiments after 24 and 48 hours treatment stained with Annexin V.
Figure 5:
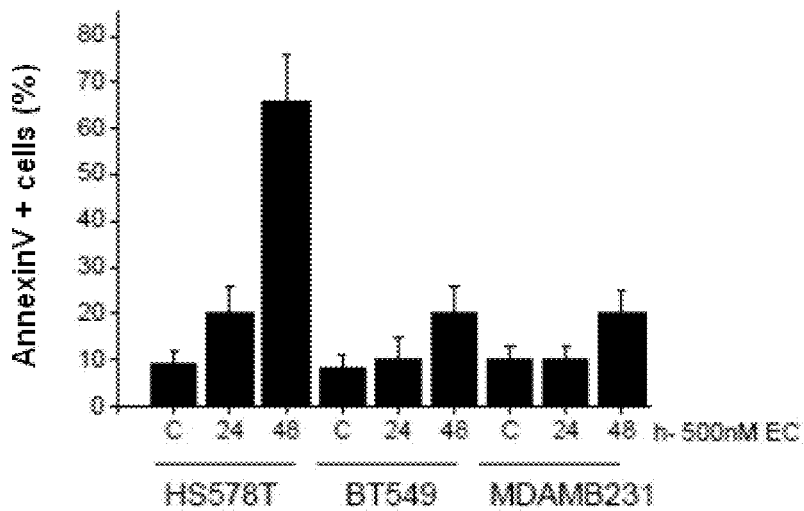
Figure 6:
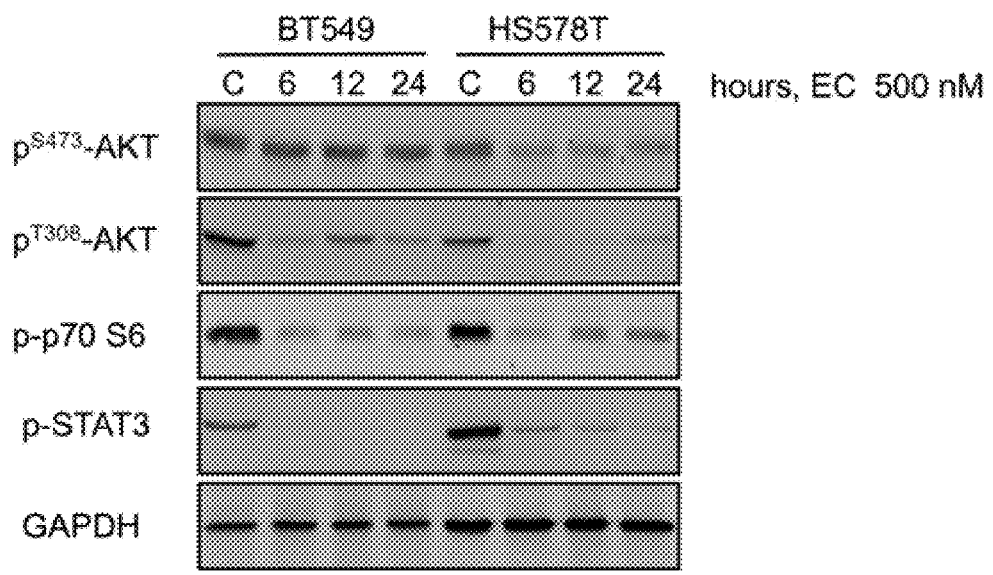
FIG. 6. Inhibition of components of the PI3K/mTOR/AKT and JAK/STAT pathway by Formula (III) (EC) (500 nM) after initial treatment (C) to 24 h after treatment, determined using a Western Blot of phosphorylated AKT (pS473-AKT, pT308-AKT), p70 S6 (p-p70 S6) and STAT3 (p-STAT3) normalized to GADPH.

Annexin V staining was also used to explore the effect of Formula (III) on apoptosis, whereby an increase at 48 hours, more evident in HS578T was observed (FIG. 5B). Similarly, the activation (phosphorylation) of receptor tyrosine kinases and intracellular kinases by Formula (III) was confirmed by Western Blot, whereby it was shown that said compound inhibits components of the PI3K/mTOR/AKT and JAK/STAT pathway (FIG. 6).

Figure 7:
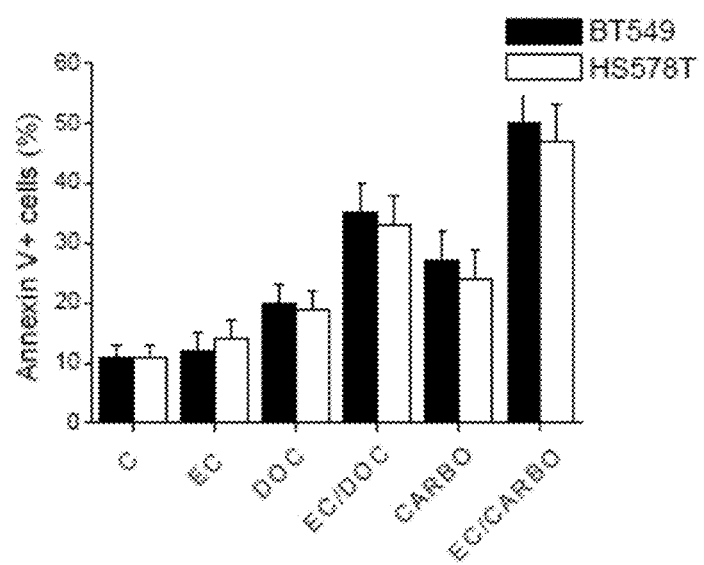
FIG. 7. Apoptotic effect on BT549 (black bars) and HS578T (white bars) cells of Formula (III) (EC), docetaxel (DOC), carboplatin (CARBO), or combinations thereof of the former with docetaxel (EC/DOC) or carboplatin (EC/CARBO) vs. a control (C) determined as a percentage of Annexin V-expressing cells after 48 hours.

The effect of the combination of cancer chemotherapy agents, such as docetaxel and carboplatin with compounds according to present invention, such as Formula (III), on apoptosis was evaluated. The administration of Formula (III) with carboplatin clearly induced apoptosis at 48 h (cf. FIG. 7). A similar, but less evident, effect was observed with docetaxel (cf. FIG. 7). These findings suggest that the addition of some chemotherapies to Formula (III) produced an increase in cell death that was not obtained with the kinase inhibitor alone.

As DNA damage agents such as platinum compounds and tubulin-targeting agents such as taxanes induce apoptosis by producing breaks in DNA strands, the effect of these combinations on pγH2AX, a marker of double strand break [FEBS Lett. 2010; 584:3717-3724], were investigated.

Figure 8:
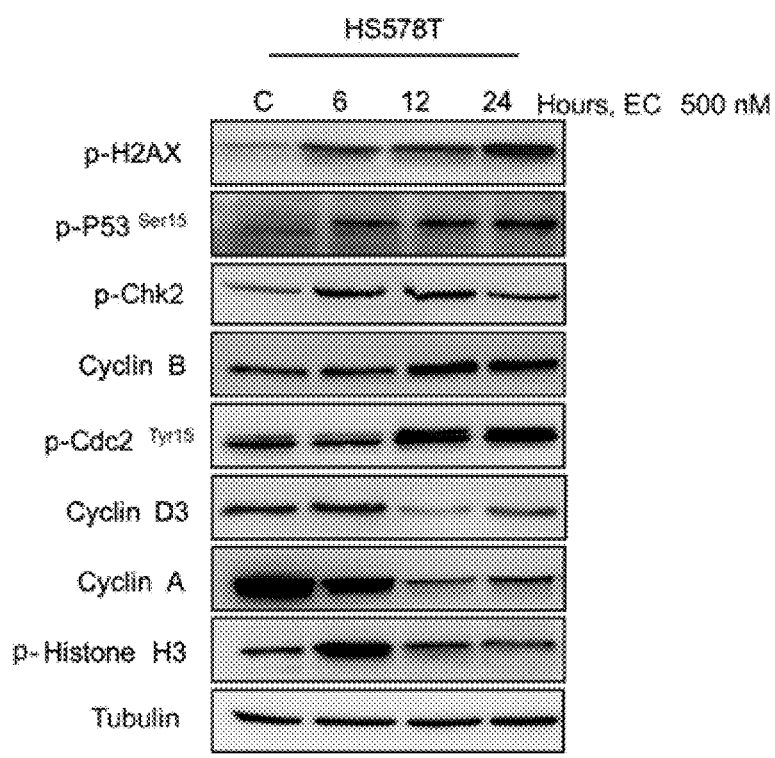
FIG. 8. DNA damaging effect of Formula (III) (EC) (500 nM) determined using a Western Blot of phosphorylated γH2AX (p-H2AX), p53 (p-P53), Chk2 (p-Chk2), Cdc2 (p-Cdc2) and histone H3 (p-Histone H3), as well as cyclins A, B and D3 as markers of said damage vs. tubulin in HS578T cells after initial treatment (C) to 24 h after treatment.

Among reasons that produce an arrest at G2/M phase is the presence of lesions in the DNA and the subsequent intent to repair and maintain its integrity. To investigate if the molecular explanation behind the inhibition of the G2/M transition is secondary to DNA damage, the levels of phosphorylated γH2AX were analyzed. It is known that this protein is required for checkpoint-mediated cell cycle arrest and DNA repair following double-stranded DNA breaks. Treatment with Formula (III) in HS578T showed an increase in the phosphorylated levels of γH2AX in a time dependent manner (FIG. 8). In response to DNA double-strand breaks (DSBs), ATM phosphorylates multiple substrates including, Chk2, p53, and γH2AX. It was observed that Formula (III) induced the phosphorylation of p53 and chk2, suggesting that Formula (III) induces G2/M arrest by producing DNA damage. The analyses of cell cycle proteins also showed that cyclin D and Cyclin A, regulators of the G1/S phase, were down-regulated after treatment with Formula (III). The observed increase in Cyclin B and p-Cdc2, confirmed the arrest at G2 (FIG. 8). Overall, these results show that treatment with Formula (III) induces DNA damage that causes cell cycle arrest in an attempt by the cell to maintain DNA integrity.

Figure 9:
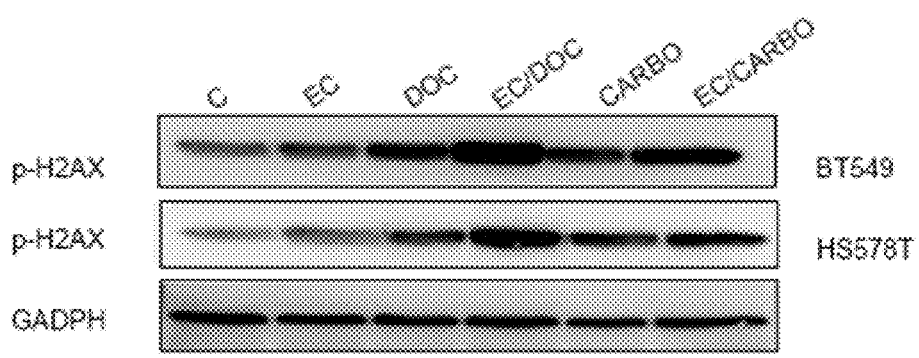
FIG. 9. DNA damaging effect of Formula (III) (EC), docetaxel (DOC), carboplatin (CARBO), or combinations thereof of the former with docetaxel (EC/DOC) or carboplatin (EC/CARBO) vs. a control (C) determined using a Western Blot of pγH2AX (p-H2AX) expression as a marker of said damage in BT549 (upper) and HS578T (middle) cells, normalized to GADPH expression.

As shown in FIG. 9 administration of Formula (III) with docetaxel or carboplatin increased pγH2AX compared with each agent given alone, thus demonstrating that the concomitant administration of both drugs increases the effect on DNA integrity.

In the experiments disclosed herein, doses of the drug in the nanomolar range were able to produce growth inhibition and a decrease in colony formation in a panel of TNBC cell lines at the same dose that inhibited efficiency of the mentioned routes. When combined with chemotherapies, Formula (III) produced a synergistic effect with, in particular, platinum compounds and docetaxel, thus rendering these agents clinically applicable. Of note, these two chemotherapies are milestones in the treatment of this disease.

When the mechanism of action was evaluated, administration of Formula (III) at short times was observed to induce DNA damage measured by the phosphorylation of γH2AX, and of other proteins including the phosphorylated form of p53 and Chk2; all downstream effectors of ATM and ATR in response to DNA insults [Nature reviews 2000; 1: 179-186, Proc. Natl. Acad. Sci. U.S.A 2000; 97: 10389-10394]. At longer times an increased expression of genes involved in DNA repair was observed; genes that probably were synthesized in response to a DNA insult. This observation was confirmed by RT-PCR of the upregulated genes including BRCA2, BRCA1, DDB2, FANCE, LIG4, GADD45, PRMT6, RAD52 or XPA, among others. The increased expression of apoptosis that was observed at 48 hours suggested that cells unable to repair DNA underwent cell death, and this effect was reinforced when Formula (III) was given in combination with chemotherapy.

Globally, combination of the kinase inhibitors of present invention with chemotherapy agents produced an increase in apoptosis secondary to an induction of DNA damage. In addition, Formula (III) synergizes with chemotherapy agents currently used in the treatment of TNBC, and such synergic combinations have been shown to be stable in in vivo model solutions, thereby rendering said synergic combinations suitable for use in the clinical setting and hence, industrially applicable.

The invention claimed is:

1. A composition comprising
   a) a compound of Formula (III)

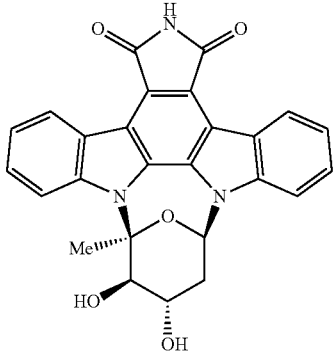

Formula (III)

and
   b) at least one chemotherapeutic agent selected from carboplatin, docetaxel and olaparib.

2. The composition according to claim 1, wherein the at least one chemotherapeutic agent is carboplatin.

3. The composition according to claim 1, wherein the at least one chemotherapeutic agent is docetaxel.

4. The composition according to claim 1, wherein the at least one chemotherapeutic agent is olaparib.

5. The composition according to claim 1, wherein said composition is a pharmaceutical composition.

6. A method of treating breast cancer in a patient, said method comprising administering to a patient in need thereof of an effective dose of the composition of claim 1.

7. A method for producing a pharmaceutical composition, which comprises mixing:
   a) a compound of Formula (III)

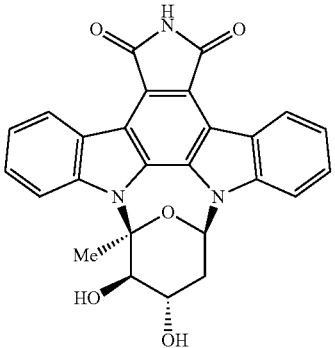

Formula (III)

and
   b) at least one chemotherapeutic agent selected from carboplatin, docetaxel and olaparib.

* * * * *